US012338236B2

(12) United States Patent
Nirogi et al.

(10) Patent No.: US 12,338,236 B2
(45) Date of Patent: Jun. 24, 2025

(54) BENZOISOTHIAZOLE AND BENZOISOXAZOLE COMPOUNDS FOR THE TREATMENT OF MENTAL DISORDERS

(71) Applicant: SUVEN LIFE SCIENCES LIMITED, Hyderabad-Telangana (IN)

(72) Inventors: Ramakrishna Nirogi, Hyderabad (IN); Anil Karbhari Shinde, Hyderabad (IN); Abdul Rasheed Mohammed, Hyderabad (IN); Kumar Bojja, Hyderabad (IN); Rajesh Kumar Badange, Hyderabad (IN); Ramkumar Subramanian, Hyderabad (IN); Pradeep Jayarajan, Hyderabad (IN); Vijay Benade, Hyderabad (IN); Venkateswarlu Jasti, Hyderabad (IN)

(73) Assignee: SUVEN LIFE SCIENCES LIMITED, Hyderabad-Telangana (IN)

( * ) Notice: Subject to any disclaimer, the term of this patent is extended or adjusted under 35 U.S.C. 154(b) by 0 days.

(21) Appl. No.: 18/832,280

(22) PCT Filed: Jan. 27, 2023

(86) PCT No.: PCT/IB2023/050711
§ 371 (c)(1),
(2) Date: Jul. 23, 2024

(87) PCT Pub. No.: WO2023/144764
PCT Pub. Date: Aug. 3, 2023

(65) Prior Publication Data
US 2025/0101014 A1    Mar. 27, 2025

(30) Foreign Application Priority Data

Jan. 29, 2022 (IN) .............................. 202241004969

(51) Int. Cl.
| | | |
|---|---|---|
| *C07D 417/14* | (2006.01) | |
| *A61K 31/454* | (2006.01) | |
| *A61K 31/4545* | (2006.01) | |
| *A61K 31/496* | (2006.01) | |
| *A61K 31/497* | (2006.01) | |
| *C07D 413/14* | (2006.01) | |

(52) U.S. Cl.
CPC .......... *C07D 417/14* (2013.01); *A61K 31/454* (2013.01); *A61K 31/4545* (2013.01); *A61K 31/496* (2013.01); *A61K 31/497* (2013.01); *C07D 413/14* (2013.01)

(58) Field of Classification Search
CPC .. C07D 417/14; C07D 413/14; A61K 31/454; A61K 31/4545; A61K 31/496; A61K 31/497
See application file for complete search history.

(56) References Cited

U.S. PATENT DOCUMENTS

| | | | |
|---|---|---|---|
| 5,958,923 A | 9/1999 | Hellendahl et al. | |
| 6,090,807 A | 7/2000 | Hellendahl et al. | |
| 6,127,357 A * | 10/2000 | Cliffe ................... | C07D 277/46 514/254.01 |
| 6,242,448 B1 | 6/2001 | Kelly et al. | |
| 2014/0024656 A1 | 1/2014 | Zhang et al. | |

FOREIGN PATENT DOCUMENTS

| | | |
|---|---|---|
| EP | 0512755 A2 | 11/1992 |
| JP | H07258252 | 10/1995 |
| WO | 94/27996 A1 | 12/1994 |
| WO | 97/40038 A1 | 10/1997 |
| WO | 97/47302 A1 | 12/1997 |
| WO | 2001017993 A1 | 3/2001 |
| WO | 2002066469 A2 | 8/2002 |
| WO | 2003074518 A1 | 9/2003 |
| WO | 2004041793 A1 | 5/2004 |
| WO | 2007026959 A2 | 3/2007 |
| WO | 2012130183 A1 | 10/2012 |
| WO | 2020156312 A1 | 8/2020 |

OTHER PUBLICATIONS

J. Cummings, et al. (2022), CNS Spectrums 27(1), 7-15. doi.org/10.1017/S1092852920001765. (Year: 2022).*
Japanese Patent Office/World Intellectual Property Organization, "JP1995258252—Thiazole Compound and Salt Thereof", published as 1995258252 on Oct. 9, 1995 (Abstract only). (2 pages).
Xu Mingshuo et al, "Synthesis and biological evaluation of a series of novel pyridinecarboxamides as potential multi-receptor antipsychotic drugs", Bioorganic & Medicinal Chemistry Letters, 2018, https://doi.org/10.1016/j.bmcl.2018.01.038 (6 pages). Article In Press.
Nasrallah, "Atypical antipsychotic-induced metabolic side effects: insights from receptor-binding profiles" Molecular Psychiatry (2008) 13:27-35.
Cutler et al., "Four-Week, Double-Blind, Placebo- and Ziprasidone-Controlled Trial of Iloperidone in Patients With Acute Exacerbations of Schizophrenia" J. Clin. Psychopharmacol. Apr. 2008; 28(2 Suppl. 1):S20-28.
International Bureau of WIPO, "International Preliminary Report on Patentability" mailed Aug. 8, 2024 in PCT Appln. No. PCT/IB2023/050711.

(Continued)

*Primary Examiner* — Medhanit W Bahta
*Assistant Examiner* — Manahil Mirghani Ali Abdalhameed
(74) *Attorney, Agent, or Firm* — IPHORGAN LTD; Valerie Neymeyer-Tynkov

(57) ABSTRACT

The present invention relates to substituted heterocyclic compounds represented by the general formula (I), or their isotopic forms, stereoisomers, or pharmaceutically acceptable salts thereof. The present invention also describes the method of making such compounds, pharmaceutical compositions comprising such compounds and their use in the treatment of central nervous system disorders.

5 Claims, 2 Drawing Sheets

(56) References Cited

OTHER PUBLICATIONS

European Patent Office, "International Search Report" mailed Mar. 30, 2023 in PCT Appln. No. PCT/IB2023/050711.
European Patent Office, "Written Opinion" mailed Mar. 30, 2023 in PCT Appln. No. PCT/IB2023/050711.
Galletly et al., "Royal Australian and New Zealand College of Psychiatrists clinical practice guidelines for the management of schizophrenia and related disorders" Austr. N.Z. J. Psychiatry (2016) 50(5):410-472.

* cited by examiner

Data represents mean ± SEM of distance travelled (cm), *P<0.001, **P<0.0001 vs. amphetamine (2.5 mg/kg, i.p.), one way ANOVA followed by Dunnett's multiple comparisons test (n=8)

Data represents mean ± SEM of latency to fall (s), **P<0.01, vs. vehicle, one way ANOVA followed by Dunnett's multiple comparisons test (n=8)

Results are mean ± SEM (n=5/ group). ^^^$p<0.001$ Vs vehicle alone (Unpaired t test); ***$p<0.001$ Vs reserpine (Dunnett's Post test)

BENZOISOTHIAZOLE AND BENZOISOXAZOLE COMPOUNDS FOR THE TREATMENT OF MENTAL DISORDERS

CROSS REFERENCE TO RELATED APPLICATIONS

This application is a national stage completion application of PCT Application No. PCT/IB2023/050711, filed Jan. 27, 2023, and claims priority from India application No. 202241004969, filed Jan. 29, 2022. Each of these applications is incorporated by reference herein in its entirety.

FIELD OF THE INVENTION

The present invention relates to substituted heterocyclic compounds represented by the general formula (I), or their isotopic forms, stereoisomers, or pharmaceutically acceptable salts thereof. The present invention also describes the method of making such compounds, pharmaceutical compositions comprising such compounds and their use in the treatment of central nervous system diseases or disorders.

BACKGROUND OF THE INVENTION

Despite the number of different antipsychotics commercially available, mental disorders like schizophrenia and psychosis, remains a complex and difficult disorder to treat. In clinical practice, the heterogeneity in individual patient response in terms of both efficacy and tolerability to different agents is at times astonishing. This leads to the common practice of switching medications, one after the other, in order to find the best fit and where adherence can be maximized.

First-generation typical antipsychotics like haloperidol (antagonists at dopamine $D_2$ receptors of the striatum) are quite useful in controlling positive symptoms, but they lack a consistent response to long-term efficacy for negative symptoms and cognitive impairments and cause the extrapyramidal side effects (EPS) which nearly nullify the therapeutic outcomes. The second generation of atypical antipsychotics, led by clozapine, has provided a broader range of therapeutic outcomes by being effective on both positive and negative symptoms and by causing fewer extra-pyramidal side effects. These new agents appeared to cause a risk for metabolic syndrome, including diabetes, weight gain, and hyperlipidemia.

Atypical antipsychotics like Iloperidone, Ziprasidone, Risperidone and Paliperidone provide antipsychotic efficacy with a lower risk of EPS than typical antipsychotics, however, these drugs appear to be associated with varying degrees of metabolic adverse effects, such as weight gain, impaired glucose metabolism, dyslipidemia and in some cases, more serious morbidity, such as cardiovascular disease (*Molecular Psychiatry* (2008) 13, 27-35; *J Clin Psychopharmacol.* 2008 April; 28 (2 Suppl 1): S20-8).

WO2020156312 discloses compounds having $D_3$ receptor agonistic and 5-$HT_{2A}$ receptor inhibitory activity.

WO2003074518 discloses thiazole derivatives of formula (I) as $D_2$ and 5-$HT_{1A}$ receptor ligands, particularly agonists of $D_2$ and 5-$HT_{1A}$ receptors.

U.S. Pat. No. 6,242,448B1 discloses 4-(arylpiperazin-1-yl) oxazole derivatives which are agonists and antagonists of the 5$HT_{1A}$ receptor subtype.

U.S. Pat. No. 5,958,923 discloses thiazole and thiadiazole compounds which are selective ligands of dopamine $D_3$ receptor and have a low affinity for the $D_2$ receptor.

U.S. Pat. No. 6,090,807 discloses heterocyclic compounds which are selective ligands of dopamine $D_3$ receptor and have a low affinity for the $D_2$ receptor.

WO2007026959 discloses a novel compound that has dopamine $D_2$ receptor partial agonist activity, serotonin 5-$HT_{2A}$ receptor antagonist activity, and adrenaline $\alpha_1$ receptor antagonist activity and further has serotonin uptake inhibitory effect.

WO2012130183 discloses [1,3,4]oxadiazole derivatives that have higher affinities for dopamine $D_2$, $D_3$, 5-$HT_{1A}$ and 5-$HT_{2A}$ receptors, for the treatment of psychoneurosis.

JPH07258252 discloses thiazole compounds have binding affinity to dopamine $D_2$ receptor, serotonin 5-$HT_2$, and adrenergic $\alpha_1$ receptor.

EP0512755A2 discloses compounds that selectively bind to receptors of 5-$HT_{1A}$ type to a much greater extent than they bind to $\alpha_1$ and $D_2$ receptors. These compounds may exhibit 5-$HT_{1A}$ receptor antagonistic activity.

WO2004041793 discloses phenylalkyl and pyridylalkylpiperazine derivatives that have activity as an antagonist of dopamine $D_2$ receptor and serotonin 5-$HT_{2A}$ receptor.

WO2002066469 discloses novel heterocyclic amide derivatives as dopamine $D_3$ receptor modulators for the treatment of central nervous system disorders.

WO2001017993 discloses alkylpiperidinylbenzo[d]isoxazole derivatives exert action on the central nervous system and have primarily psychotropic activity.

WO94/27996A1 discloses 1,2,5-thiadiazole derivatives that have a high affinity for 5-$HT_2$, dopamine $D_1$, and $D_2$ receptors or a combination of these, useful for the treatment of CNS system, cardiovascular system and/or gastrointestinal disorders.

WO97/47302 discloses tetrahydropiperidinyl- and piperidinyl-indoles and benzothiazoles of inhibition of serotonin reuptake in mammals.

WO97/40038 discloses piperidine and pyrrolidine derivatives act as 5-$HT_{1A}$ receptor antagonists and exhibit 5-HT reuptake-inhibiting actions.

Xu et al describe pyridine carboxamides compounds as potent multi-receptor antipsychotics. These compounds have good activity on dopamine $D_2$, serotonin 5-$HT_{1A}$ and 5-$HT_{2A}$ receptors, and exhibited low potency for $\alpha_{1A}$, $H_1$ and 5-$HT_{2C}$ receptors (*Bioorganic & Medicinal Chemistry Letters* 28 (2018) 606-611).

Although the prior arts disclose typical and atypical antipsychotic agents that act on single or multi-targets, they are associated with side effects such as EPS, dyslipidemia, weight gain, diabetes, and QT interval prolongation, with no or limited effect on negative symptoms and cognitive dysfunction. Additionally, a high level of non-adherence is observed in patients, mainly because of side-effects such as movement disorders, metabolic, and cardiometabolic side effects. Poor recovery and relapse of symptoms have been linked to poor treatment response (*Aust N Z J Psychiatry* 50(5) 410-472). Therefore, there is a need for the development of new antipsychotics with reduced side-effects and improved tolerability and safety as compared with known typical and atypical antipsychotics.

The present invention discloses compounds targeting 5-$HT_{1A}$ receptor agonism in addition to partial agonistic activity at dopamine $D_2$ and antagonist activity at serotonin 5-$HT_{2A}$ receptor as 5-$HT_{1A}$ receptor agonism can improve the negative symptoms and cognitive impairment of patients, and can also improve the positive symptoms indirectly and alleviate EPS.

SUMMARY OF THE INVENTION

In first aspect, the present invention relates to a compound of formula (I),

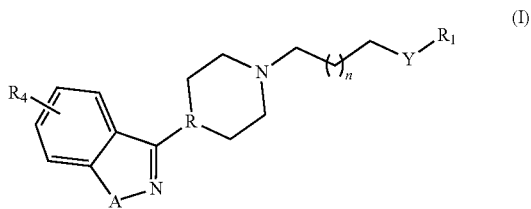

or an isotopic form, a stereoisomer, or a pharmaceutically acceptable salt thereof,
wherein,
A is O or S;
R is N or CH;
Y is selected from —$CH_2$—, —O—, NH, or —$N(C_{1-4}$ alkyl)-;
n is an integer from 0 to 2;
$R_1$ is selected from:

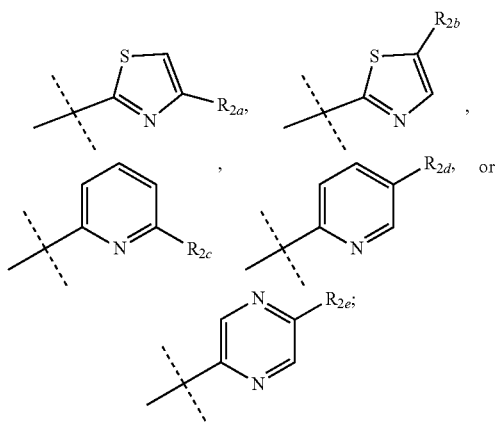

wherein, $R_{2a}$, $R_{2b}$, $R_{2c}$, $R_{2d}$ and $R_{2e}$ are each independently selected from:

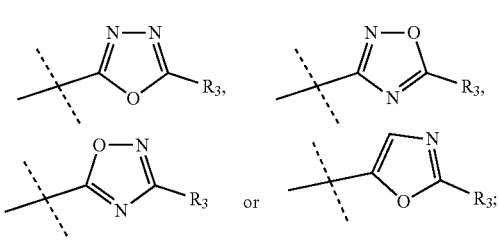

"------" represents the point of attachment;
$R_3$ at each occurrence is independently selected from hydrogen, —$(C_{1-4})$alkyl, or —$(C_{3-6})$cycloalkyl; and
$R_4$ is selected from hydrogen, halogen, —$(C_{1-4})$alkyl, —$(C_{3-6})$cycloalkyl or hydroxy-$(C_{1-4})$alkyl.

In another aspect, the present invention relates to processes for the preparation of the compound of formula (I), or an isotopic form, a stereoisomer, or a pharmaceutically acceptable salt thereof.

In another aspect, the present invention relates to a method of treating disease or disorder selected from schizophrenia, psychosis, bipolar disorder, mood disorders, depression, anxiety, sleep disorders, sexual disorders, drug dependency withdrawal symptoms, attention deficit hyperactivity disorder, neuropsychiatric disorders associated with Alzheimer's disease, Parkinson's disease, Lewy body dementia, Frontotemporal dementia, and vascular dementia, comprising administering to a patient in need thereof, a therapeutically effective amount of the compound of formula (I), or an isotopic form, a stereoisomer, or a pharmaceutically acceptable salt thereof.

In another aspect, the present invention relates to the compound of formula (I), or an isotopic form, a stereoisomer, or a pharmaceutically acceptable salt thereof for use in the treatment of disease or disorder selected from schizophrenia, psychosis, bipolar disorder, mood disorders, depression, anxiety, sleep disorders, sexual disorders, drug dependency withdrawal symptoms, attention deficit hyperactivity disorder, neuropsychiatric disorders associated with Alzheimer's disease, Parkinson's disease, Lewy body dementia, Frontotemporal dementia, and vascular dementia.

In another aspect, the present invention relates to use of the compound of formula (I), or an isotopic form, a stereoisomer, or a pharmaceutically acceptable salt thereof for the manufacture of a medicament for the treatment of disease or disorder selected from schizophrenia, psychosis, bipolar disorder, mood disorders, depression, anxiety, sleep disorders, sexual disorders, drug dependency withdrawal symptoms, attention deficit hyperactivity disorder, neuropsychiatric disorders associated with Alzheimer's disease, Parkinson's disease, Lewy body dementia, Frontotemporal dementia, and vascular dementia.

In another aspect, the present invention relates to the compound of formula (I), or an isotopic form, a stereoisomer, or a pharmaceutically acceptable salt thereof for use as a partial agonist of dopamine $D_2$ receptor, an antagonist of 5-Hydroxytryptamine 2A receptor, and partial agonist of 5-Hydroxytryptamine 1A receptor.

In another aspect, the present invention relates to a pharmaceutical composition comprising a therapeutically effective amount of at least one of the compound of formula (I), or an isotopic form, a stereoisomer, or a pharmaceutically acceptable salt thereof, and pharmaceutically acceptable excipients or carriers.

DETAILED DESCRIPTION OF THE INVENTION

Figure 1:
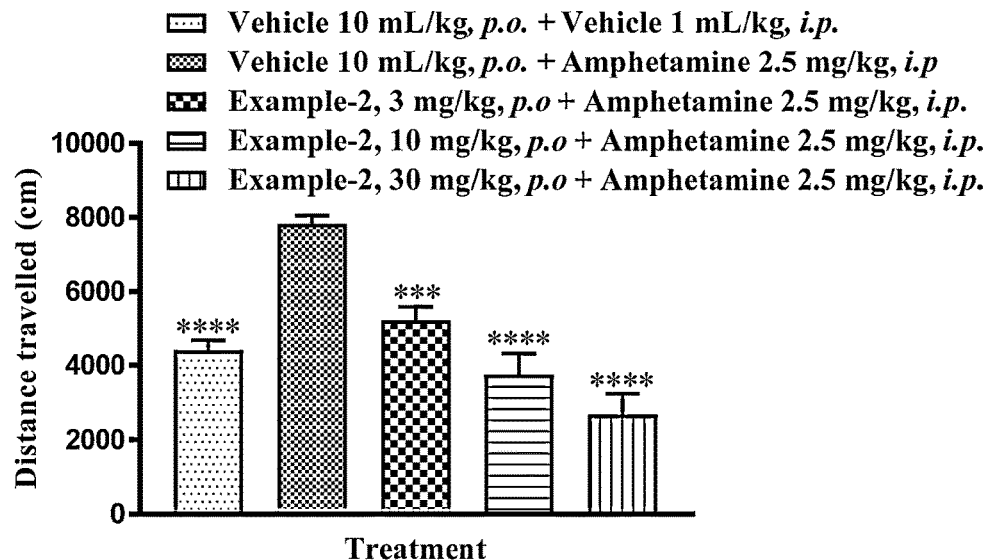
FIG. 1: Effect of Example-2 on amphetamine-induced hyperlocomotion

Unless otherwise stated, the following terms used in the specification and claims have the meanings given below:

The term, "—$(C_{1-4})$alkyl" as used herein refers to branched or linear chain aliphatic hydrocarbon containing from one to four carbon atoms. Examples of —$(C_{1-4})$alkyl include methyl, ethyl, n-propyl, isopropyl, n-butyl, isobutyl, sec-butyl and tert-butyl.

The term, "—$(C_{3-6})$cycloalkyl" as used herein refers to a saturated monocyclic hydrocarbon ring containing from three to six carbon atoms. Examples of —($C_{3-6}$)cycloalkyl group include cyclopropyl, cyclobutyl, cyclopentyl and cyclohexyl.

The term, "hydroxy-($C_{1-4}$)alkyl" as used herein refers to —($C_{1-4}$)alkyl as defined above wherein one or more hydrogen of the same or different carbon atoms is substituted with hydroxy group. Examples of hydroxy-($C_{1-4}$)alkyl group include hydroxymethyl, hydroxyethyl, hydroxypropyl, and hydroxybutyl.

The term, "halogen" as used herein refers to fluorine, chlorine, bromine or iodine. Preferably, halogen is fluorine, chlorine or bromine.

The term, "isotopic form" as used herein refers to the compound of formula (I) wherein one or more atoms of the compound of formula (I) are substituted by their respective isotopes. For example, isotopes of hydrogen include $^2$H (deuterium) and $^3$H (tritium).

The term, "stereoisomer" as used herein refers to isomers of the compound of formula (I) that differ in the arrangement of their atoms in space. Compounds disclosed herein may exist as a single stereoisomer, racemates and/or mixtures of enantiomers and/or diastereomers. All such single stereoisomer, racemates and mixtures thereof are intended to be within the scope of the present invention.

The term "neuropsychiatric disorders", refer to a heterogeneous group of non-cognitive symptoms and behaviors occurring in patients with Alzheimer's disease, Parkinson's disease, Lewy body dementia, Frontotemporal dementia, and vascular dementia. Neuropsychiatric disorders include domains like agitation/aggression, delusions and/or hallucinations, aberrant motor behavior, aberrant vocalizations, anxiety, elation/euphoria, irritability, depression/dysphoria, apathy, disinhibition, sleep and night time behavior or appetite and eating change.

The phrase, "pharmaceutically acceptable salt" as used herein refers to a salt of the active compound i.e. the compound of formula (I), and is prepared by reaction with the appropriate acid or acid derivative, depending on the particular substituents found on the compounds described herein.

The phrase, "therapeutically effective amount" is defined as an amount of a compound of the present invention that (i) treats the particular disease, condition or disorder (ii) eliminates one or more symptoms of the particular disease, condition or disorder (iii) delays the onset of one or more symptoms of the particular disease, condition or disorder described herein.

The term, "patient" as used herein refers to an animal. Preferably the term "patient" refers to a mammal. The term mammal includes animals such as mice, rats, dogs, rabbits, pigs, monkeys, horses, pigeons, *Xenopus laevis*, zebrafish, guinea pigs and humans. More preferably the patient is human.

Embodiments

The present invention encompasses all the compounds described by the compound of formula (I) without any limitation, however, preferred aspects and elements of the invention are discussed herein in the form of following embodiments.

In one embodiment, the present invention relates to the compound of formula (Ia) derived from the compound of formula (I),

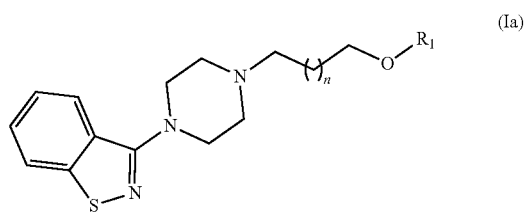

or an isotopic form, a stereoisomer, or a pharmaceutically acceptable salt thereof,
wherein:
n is an integer from 0 to 2;
$R_1$ is selected from:

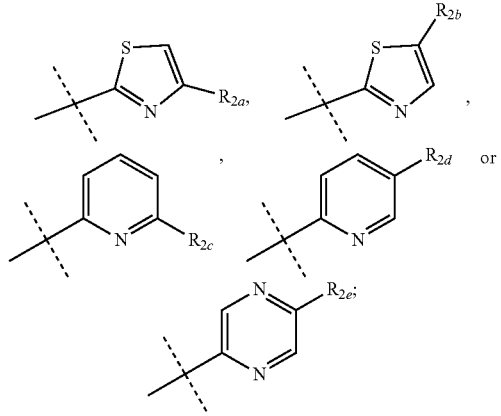

wherein, $R_{2a}$, $R_{2b}$, $R_{2c}$, $R_{2d}$, and $R_{2e}$ are each independently selected from:

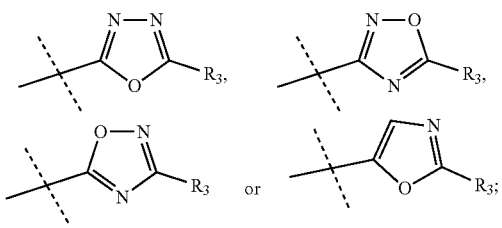

"------" represents the point of attachment; and
$R_3$ at each occurrence is independently selected from hydrogen, —($C_{1-4}$)alkyl, or —($C_{3-6}$)cycloalkyl.

In another embodiment, the present invention relates to the compound of formula (Ib) derived from the compound of formula (I),

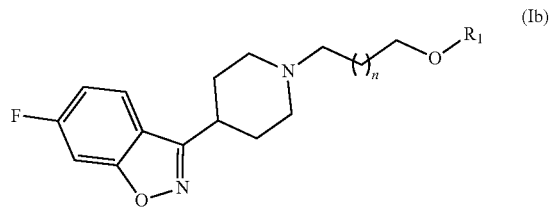

or an isotopic form, a stereoisomer, or a pharmaceutically acceptable salt thereof, wherein:

n is an integer from 0 to 2;

$R_1$ is selected from:

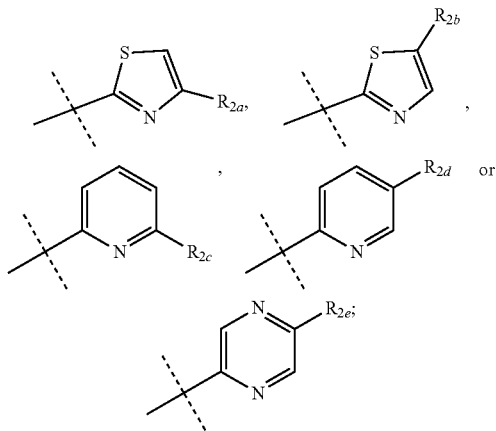

wherein, $R_{2a}$, $R_{2b}$, $R_{2c}$, $R_{2d}$, and $R_{2e}$ are each independently selected from:

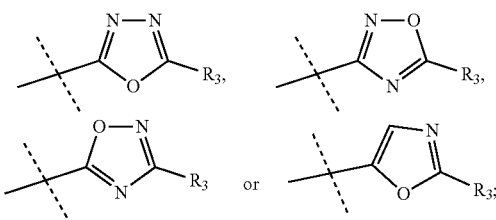

"------" represents the point of attachment; and $R_3$ at each occurrence is independently selected from hydrogen, —$(C_{1-4})$alkyl, or —$(C_{3-6})$cycloalkyl.

In some embodiments of the compound of formula (1b), wherein $R_1$ is selected from:

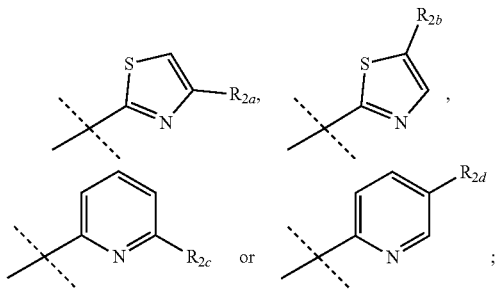

wherein, $R_{2a}$, $R_{2b}$, $R_{2c}$ and $R_{2d}$ are each independently selected from:

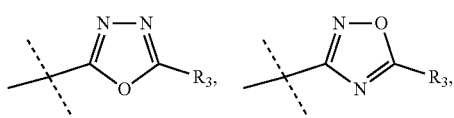

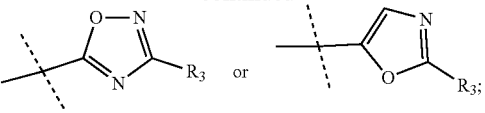

wherein $R_3$ at each occurrence is independently selected from hydrogen or —$(C_{1-4})$alkyl.

In another embodiment, the compound of formula (I), or a pharmaceutically acceptable salt thereof is selected from the group consisting of:

3-(4-{3-[4-(5-Methyl-[1,3,4]oxadiazol-2-yl)-thiazol-2-yloxy]-propyl}-piperazin-1-yl)-benzo[d]isothiazole;

3-(4-{2-[4-(5-Methyl-[1,3,4]oxadiazol-2-yl)-thiazol-2-yloxy]-ethyl}-piperazin-1-yl)-benzo[d]isothiazole;

3-(4-{3-[4-(5-Cyclopropyl-[1,3,4]oxadiazol-2-yl)-thiazol-2-yloxy]-propyl}-piperazin-1-yl)-benzo[d]isothiazole;

3-(4-{3-[5-(5-Methyl-[1,3,4]oxadiazol-2-yl)-thiazol-2-yloxy]-propyl}-piperazin-1-yl)-benzo[d]isothiazole;

3-(4-{3-[4-(5-Methyl-[1,2,4]oxadiazol-3-yl)-thiazol-2-yloxy]-propyl}-piperazin-1-yl)-benzo[d]isothiazole;

3-(4-{3-[4-(3-Methyl-[1,2,4]oxadiazol-5-yl)-thiazol-2-yloxy]-propyl}-piperazin-1-yl)-benzo[d]isothiazole;

3-{4-[3-(4-Oxadiazol-5-yl-thiazol-2-yloxy)-propyl]-piperazin-1-yl}-benzo[d]isothiazole;

3-(4-{3-[6-(5-Methyl-[1,2,4]oxadiazol-3-yl)-pyridin-2-yloxy]-propyl}-piperazin-1-yl)-benzo[d]isothiazole;

3-(4-{3-[5-(5-Methyl-[1,2,4]oxadiazol-3-yl)-pyridin-2-yloxy]-propyl}-piperazin-1-yl)-benzo[d]isothiazole;

3-(4-{3-[5-(5-Methyl-[1,2,4]oxadiazol-3-yl)-pyrazin-2-yloxy]-propyl}-piperazin-1-yl)-benzo[d]isothiazole;

3-{4-[3-(5-Oxazol-5-yl-pyridin-2-yloxy)-propyl]-piperazin-1-yl}-benzo[d]isothiazole;

6-Fluoro-3-(1-{3-[4-(5-methyl-[1,3,4]oxadiazol-2-yl)-thiazol-2-yloxy]-propyl}-piperidin-4-yl)-benzo[d]isoxazole;

6-Fluoro-3-(1-{3-[5-(5-methyl-[1,3,4]oxadiazol-2-yl)-thiazol-2-yloxy]-propyl}-piperidin-4-yl)-benzo[d]isoxazole;

6-Fluoro-3-(1-{3-[4-(5-methyl-[1,2,4]oxadiazol-3-yl)-thiazol-2-yloxy]-propyl}-piperidin-4-yl)-benzo[d]isoxazole;

6-Fluoro-3-(1-{3-[4-(3-methyl-[1,2,4]oxadiazol-5-yl)-thiazol-2-yloxy]-propyl}-piperidin-4-yl)-benzo[d]isoxazole;

6-Fluoro-3-{1-[3-(4-oxazol-5-yl-thiazol-2-yloxy)-propyl]-piperidin-4-yl}-benzo[d]isoxazole;

6-Fluoro-3-{1-[3-(5-oxazol-5-yl-pyridin-2-yloxy)-propyl]-piperidin-4-yl}-benzo[d]isoxazole;

3-(4-{3-[6-(5-Methyl-[1,3,4]oxadiazol-2-yl)-pyridin-2-yloxy]-propyl}-piperazin-1-yl)-benzo[d]isothiazole;

3-(4-{3-[6-(3-Methyl-[1,2,4]oxadiazol-5-yl)-pyridin-2-yloxy]-propyl}-piperazin-1-yl)-benzo[d]isothiazole;

3-{4-[3-(4-[1,2,4]oxadiazol-3-yl-thiazol-2-yloxy)-propyl]-piperazin-1-yl}-benzo[d]isothiazole; and 3-{4-[3-(6-[1,2,4]Oxadiazol-3-yl-pyridin-2-yloxy)-propyl]-piperazin-1-yl}-benzo[d]isothiazole.

In another embodiment, the compound of formula (I), or a pharmaceutically acceptable salt thereof is selected from the group consisting of:

3-(4-{3-[4-(5-Methyl-[1,3,4]oxadiazol-2-yl)-thiazol-2-yloxy]-propyl}-piperazin-1-yl)-benzo[d]isothiazole oxalate;

3-(4-{2-[4-(5-Methyl-[1,3,4]oxadiazol-2-yl)-thiazol-2-yloxy]-ethyl}-piperazin-1-yl)-benzo[d]isothiazole oxalate;

3-(4-{3-[4-(5-Cyclopropyl-[1,3,4]oxadiazol-2-yl)-thiazol-2-yloxy]-propyl}-piperazin-1-yl)-benzo[d]isothiazole oxalate;

3-(4-{3-[5-(5-Methyl-[1,3,4]oxadiazol-2-yl)-thiazol-2-yloxy]-propyl}-piperazin-1-yl)-benzo[d]isothiazole oxalate;

3-(4-{3-[4-(5-Methyl-[1,2,4]oxadiazol-3-yl)-thiazol-2-yloxy]-propyl}-piperazin-1-yl)-benzo[d]isothiazole oxalate;

3-(4-{3-[4-(3-Methyl-[1,2,4]oxadiazol-5-yl)-thiazol-2-yloxy]-propyl}-piperazin-1-yl)-benzo[d]isothiazole oxalate;

3-{4-[3-(4-Oxazol-5-yl-thiazol-2-yloxy)-propyl]-piperazin-1-yl}-benzo[d]isothiazole oxalate;

3-(4-{3-[6-(5-Methyl-[1,2,4]oxadiazol-3-yl)-pyridin-2-yloxy]-propyl}-piperazin-1-yl)-benzo[d]isothiazole oxalate;

3-(4-{3-[5-(5-Methyl-[1,2,4]oxadiazol-3-yl)-pyridin-2-yloxy]-propyl}-piperazin-1-yl)-benzo[d]isothiazole oxalate;

3-(4-{3-[5-(5-Methyl-[1,2,4]oxadiazol-3-yl)-pyrazin-2-yloxy]-propyl}-piperazin-1-yl)-benzo[d]isothiazole oxalate;

3-{4-[3-(5-Oxazol-5-yl-pyridin-2-yloxy)-propyl]-piperazin-1-yl}-benzo[d]isothiazole oxalate;

6-Fluoro-3-(1-{3-[4-(5-methyl-[1,3,4]oxadiazol-2-yl)-thiazol-2-yloxy]-propyl}-piperidin-4-yl)-benzo[d]isoxazole oxalate;

6-Fluoro-3-(1-{3-[5-(5-methyl-[1,3,4]oxadiazol-2-yl)-thiazol-2-yloxy]-propyl}-piperidin-4-yl)-benzo[d]isoxazole oxalate;

6-Fluoro-3-(1-{3-[4-(5-methyl-[1,2,4]oxadiazol-3-yl)-thiazol-2-yloxy]-propyl}-piperidin-4-yl)-benzo[d]isoxazole oxalate;

6-Fluoro-3-(1-{3-[4-(3-methyl-[1,2,4]oxadiazol-5-yl)-thiazol-2-yloxy]-propyl}-piperidin-4-yl)-benzo[d]isoxazole oxalate;

6-Fluoro-3-{1-[3-(4-oxazol-5-yl-thiazol-2-yloxy)-propyl]-piperidin-4-yl}-benzo[d]isoxazole oxalate;

6-Fluoro-3-{1-[3-(5-oxazol-5-yl-pyridin-2-yloxy)-propyl]-piperidin-4-yl}-benzo[d]isoxazole oxalate;

3-(4-{3-[6-(5-Methyl-[1,3,4]oxadiazol-2-yl)-pyridin-2-yloxy]-propyl}-piperazin-1-yl)-benzo[d]isothiazole oxalate;

3-(4-{3-[6-(3-Methyl-[1,2,4]oxadiazol-5-yl)-pyridin-2-yloxy]-propyl}-piperazin-1-yl)-benzo[d]isothiazole oxalate;

3-{4-[3-(4-[1,2,4]oxadiazol-3-yl-thiazol-2-yloxy)-propyl]-piperazin-1-yl}-benzo[d]isothiazole oxalate; and 3-{4-[3-(6-[1,2,4]Oxadiazol-3-yl-pyridin-2-yloxy)-propyl]-piperazin-1-yl}-benzo[d]isothiazole oxalate.

In another embodiment, the present invention relates to processes for the preparation of the compound of formula (I) as described herein.

Experimental Procedure

Scheme-1 depicts a general process for the preparation of the compound of formula (I), wherein X is halogen, Y is O, and A, R, R₁, R₄ and n are as defined in the first aspect.

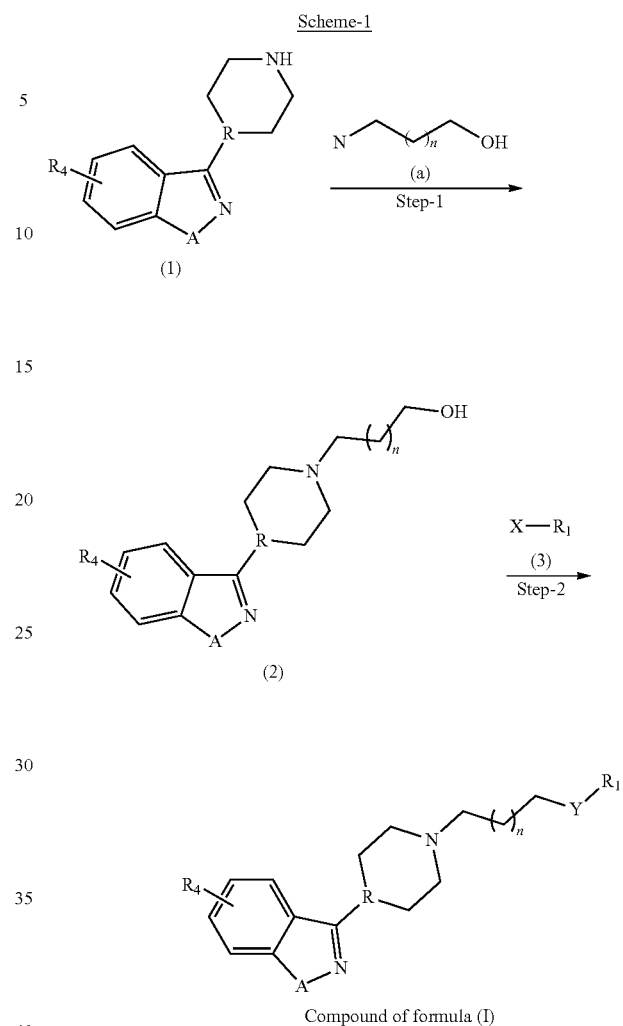

Step-1: Preparation of Compound of Formula (2)

The compound of formula (2) was prepared by reacting the compound formula (1) with formula (a) by using a base such as $K_2CO_3$, $CS_2CO_3$, or $Na_2CO_3$ in the presence of a solvent selected from acetonitrile, THF or DMF at temperature ranging from RT to 80° C. for a period of 2 to 16 h, preferably for a period of 6 h.

Step-2: Preparation of the Compound of Formula (I)

The compound of formula (I) was prepared by reacting the compound of formula (2) with a compound of formula (3) by using a base such as sodium hydride, potassium hydride, potassium tert-butoxide or sodium tert-butoxide in a solvent selected from THF, DMF, DMSO, diethylether, or 1,4-dioxane at temperature ranging from 0° C. to reflux temperature for a period of 2 to 16 h, preferably for a period of 6 h.

Scheme-2 depicts a general process for the preparation of the compound of formula (I), wherein X is halogen, Y is O, and A, R, R₁, R₄ and n are as defined in the first aspect.

Scheme-2

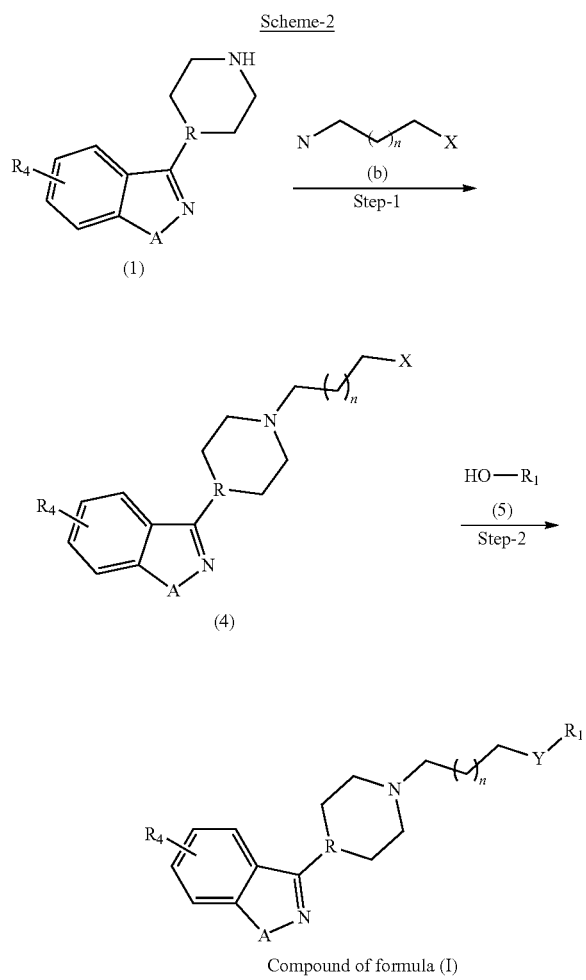

Compound of formula (I)

Scheme-3

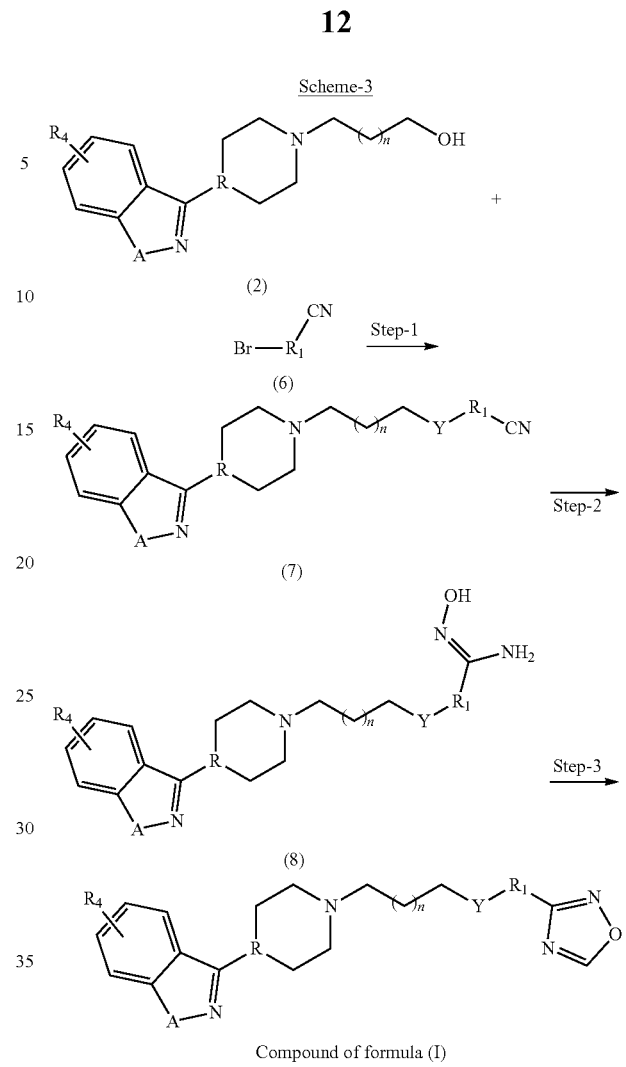

Compound of formula (I)

Step-1: Preparation of Compound of Formula (4)

The compound of formula (4) was obtained by reacting the compound of formula (1) with a compound of formula (b) in presence of a base such as $K_2CO_3$, $CS_2CO_3$, $Na_2CO_3$, KOH or NaOH and solvents selected from THF, 1,4-dioxane, dichloromethane, 1,2-dichloroethane, acetonitrile, $H_2O$ or one or two combination of above solvents at temperature ranging from RT to 90° C. preferably at RT for a period of 2-16 h.

Step-2: Preparation of the Compound of Formula (I)

The compound of formula (I) was obtained by reacting the compound formula (4) with a compound of formula (5) by using a base such as sodium hydride, potassium hydride or sodium tert-butoxide in a solvent selected from THF, DMF, DMSO, diethylether, or 1,4-dioxane at temperature ranging from 0° C. to reflux temperature for a period of 2 to 16 h, preferably for a period of 6 h.

Scheme-3 depicts a general process for the preparation of the compound of formula (I), wherein hydrogen atom of $R_1$ is substituted with [1,2,4]oxadiazol, Y is O and A, R, $R_1$, $R_4$ and n are as defined in the first aspect.

Step-1: Preparation of Compound of Formula (7)

The compound of formula (7) was obtained by reacting the compound of formula (2) with formula (6) by using a base such as $K_2CO_3$, $CS_2CO_3$, $Na_2CO_3$, KOH or NaOH and solvents selected from THF, 1,4-dioxane, dichloromethane, 1,2-dichloroethane, acetonitrile, $H_2O$ or one or two combination of above solvents at a temperature ranging from RT to 90° C., preferably at RT for a period of 2-16 h preferably for a period of 6 h.

Step-2: Preparation of Compound of Formula (8)

The compound of formula (8) was obtained by reacting the compound formula (7) with hydroxylamine hydrochloride by using a base such as $K_2CO_3$, or $CS_2CO_3$ in a solvent selected from ethanol, methanol, or isopropanol at a temperature ranging from RT to 85° C. for a period of 2-12 h, preferably for a period of 4 h.

Step-3: Preparation of the Compound of Formula (I)

The compound of formula (I) wherein hydrogen atom of $R_1$ is substituted with [1,2,4]-oxadiazole was obtained by reacting the compound formula (8) with triethyl orthoformate by using a base such as $K_2CO_3$, or $CS_2CO_3$ in a solvent such as methanol, ethanol or isopropanol at a temperature ranging from RT to 85° C. for a period of 2-12 h, preferably for a period of 4 h.

Preparation of Pharmaceutically Acceptable Salts of the Compound of Formula (I)

The compound of formula (I) can optionally be converted into its pharmaceutically acceptable salt by reaction with the appropriate acid or acid derivative. Suitable pharmaceutically acceptable salts will be apparent to those skilled in the art. The salts are formed with inorganic acids e.g., hydrochloric, hydrobromic, sulfuric, nitric or phosphoric acid, or organic acids e.g., oxalic, succinic, maleic, acetic, citric, malic, tartaric, benzoic, p-toluic, p-toluenesulfonic, benzenesulfonic acid, methanesulfonic or naphthalene sulfonic acid.

Preparation of Stereoisomer's of the Compound of Formula (I)

The stereoisomer's of the compounds of formula (I) may be prepared by one or more conventional ways presented below:
a. One or more of the reagents may be used in their optically active form.
b. Optically pure catalyst or chiral ligands along with metal catalyst may be employed in the reduction process. The metal catalyst may be rhodium, ruthenium, indium and the like. The chiral ligands may preferably be chiral phosphines.
c. The mixture of stereoisomers may be resolved by conventional methods such as forming diastereomeric salts with chiral acids, chiral amines, chiral amino alcohols or chiral amino acids. The resulting mixture of diastereomers may then be separated by methods such as fractional crystallization, chromatography and the like, which is followed by an additional step of isolating the optically active product from the resolved material salt.
d. The mixture of stereoisomers may be resolved by conventional methods such as microbial resolution, resolving the diastereomeric salts formed with chiral acids or chiral bases. Chiral acids that can be employed may be tartaric acid, mandelic acid, lactic acid, camphorsulfonic acid, amino acids and the like. Chiral bases that can be employed may be cinchona alkaloids, brucine or a basic amino acid such as lysine, arginine and the like.

In another embodiment, the suitable pharmaceutically acceptable salts of the compound of formula (I) include but are not limited to, hydrochloride, hydrobromide, oxalate, tartrate, maleate and succinate.

In another embodiment, the present invention relates the pharmaceutical compositions comprising the compound of formula (I) or an isotopic form, a stereoisomer, or a pharmaceutically acceptable salt thereof and pharmaceutically acceptable excipients or carriers. In order to use the compounds of formula (I) or their stereoisomers and a pharmaceutically acceptable salt thereof in therapy, they will normally be formulated into a pharmaceutical composition in accordance with standard pharmaceutical practice.

The pharmaceutical compositions of the present invention may be formulated in a conventional manner using one or more pharmaceutically acceptable excipients. The pharmaceutically acceptable excipients are diluents, disintegrating agents, binders, lubricants, glidants, polymers, coating agents, solvents, co-solvents, preservatives, wetting agents, thickening agents, antifoaming agents, sweetening agents, flavoring agents, antioxidants, colorants, solubilizers, plasticizer, dispersing agents and the like. Excipients are selected from microcrystalline cellulose, mannitol, lactose, pregelatinized starch, sodium starch glycolate, corn starch or derivatives thereof, povidone, crospovidone, calcium stearate, glycerylmonostearate, glycerylpalmitostearate, talc, colloidal silicon dioxide, magnesium stearate, sodium lauryl sulfate, sodium stearyl fumarate, zinc stearate, stearic acid, hydrogenated vegetable oil, gum arabica, magnesia, glucose, fats, waxes, natural or hardened oils, water, physiological sodium chloride solution, alcohols, for example, ethanol, propanol or glycerol, sugar solutions, such as glucose solutions or mannitol solutions and the like or a mixture of the various excipients.

In another embodiment, the compounds of the invention may be formulated in the form of pills, tablets, coated tablets, capsules, powder, granules, pellets, patches, implants, films, liquids, semi-solids, gels, aerosols, emulsions, elixirs and the like. Such pharmaceutical compositions and processes for preparing the same are well known in the art.

In another embodiment, the pharmaceutical composition of the present invention contains 1 to 90%, 5 to 75% or 10 to 60% by weight of the compounds of the present invention or pharmaceutically acceptable salt thereof. The amount of the compounds or its pharmaceutically acceptable salt in the pharmaceutical composition(s) can range from about 1 mg to about 500 mg, from about 5 mg to about 400 mg, from about 5 mg to about 250 mg, from about 7 mg to about 150 mg, or in any range falling within the broader range of 1 mg to 500 mg.

In another embodiment, the present invention relates to the pharmaceutical composition comprising the compound of formula (I) or an isotopic form, a stereoisomer, or the pharmaceutically acceptable salt thereof and pharmaceutically acceptable excipients for use in the treatment of disease or disorder selected from schizophrenia, psychosis, bipolar disorder, mood disorders, depression, anxiety, sleep disorders, sexual disorders, drug dependency withdrawal symptoms, attention deficit hyperactivity disorder, neuropsychiatric disorders associated with Alzheimer's disease, Parkinson's disease, Lewy body dementia, Frontotemporal dementia, and vascular dementia.

In another embodiment, the present invention relates to the method of treating disease or disorder selected from schizophrenia, psychosis, bipolar disorder, mood disorders, depression, anxiety, sleep disorders, sexual disorders, drug dependency withdrawal symptoms, attention deficit hyperactivity disorder, neuropsychiatric disorders associated with Alzheimer's disease, Parkinson's disease, Lewy body dementia, Frontotemporal dementia, and vascular dementia, comprising a step of administering to a patient in need thereof a therapeutically effective amount of the compound of formula (I), or an isotopic form, a stereoisomer or a pharmaceutically acceptable salt thereof.

In another embodiment, the present invention relates to the compound of formula (I), or an isotopic form, a stereoisomer or a pharmaceutically acceptable salt thereof for use in the treatment of disease or disorder selected from schizophrenia, psychosis, bipolar disorder, mood disorders, depression, anxiety, sleep disorders, sexual disorders, drug dependency withdrawal symptoms, attention deficit hyperactivity disorder, neuropsychiatric disorders associated with Alzheimer's disease, Parkinson's disease, Lewy body dementia, Frontotemporal dementia, and vascular dementia.

In another embodiment, the present invention relates to use of the compound of formula (I), or an isotopic form, a stereoisomer or a pharmaceutically acceptable salt thereof for the manufacture of a medicament for the treatment of disease or disorder selected from schizophrenia, psychosis, bipolar disorder, mood disorders, depression, anxiety, sleep disorders, sexual disorders, drug dependency withdrawal symptoms, attention deficit hyperactivity disorder, neuropsychiatric disorders associated with Alzheimer's disease, Parkinson's disease, Lewy body dementia, Frontotemporal dementia, and vascular dementia.

The dose of the active compounds of the invention can vary depending on factors such as age and weight of patient, nature and severity of the disease to be treated and such other factors. Therefore, any reference regarding therapeutically effective amount of the compounds of formula (I), or an isotope, stereoisomers and pharmaceutically acceptable salts thereof refer to the aforementioned factors.

The following abbreviations are used herein:

| | |
|---|---|
| $5-HT_{1A}$ | 5-Hydroxytryptamine 1A receptor |
| $5-HT_{2A}$ | 5-Hydroxytryptamine 2A receptor |
| AUC | Area under the curve |
| $C_{max}$ | Maximum concentration |
| $CaCl_2$ | Calcium chloride |
| $CDCl_3$ | Deuteratedchloroform |
| $CHCl_3$ | Chloroform |
| DOPA | Dihydroxyphenylalanine |
| DCM | Dichloromethane |
| DMF | N,N-dimethylformamide |
| DMSO | Dimethyl sulfoxide |
| $EC_{50}$ | Half maximal effective concentration |
| EDTA | Ethylenediaminetetraacetic acid |
| EtOAc | Ethyl acetate |
| EtOH | Ethanol |
| g | Grams |
| h | Hour (s) |
| $H_2O$ | Water |
| i.p | Intraperitoneal |
| $K_2CO_3$ | Potassium carbonate |
| KCl | Potassium chloride |
| KOH | Potassium hydroxide |
| LC-MS/MS | Liquid chromatography-Mass spectrometry/Mass spectrometry |
| mL | Milliliter |
| mmol | Millimoles |
| min | minute(s) |
| MeOH | Methanol |
| $MgSO_4$ | Magnesium sulfate |
| NaH | Sodium hydride |
| NaCl | Sodium chloride |
| $NaHCO_3$ | Sodium bicarbonate |
| $Na_2SO_4$ | Sodium sulphate |
| $NH_4OH$ | Ammonium hydroxide |
| p.o | Per Oral |
| $POCl_3$ | Phosphoryl chloride |
| RT | Room temperature (25° C. to 30° C.) |
| SERT | Serotonin reuptake transporter |
| THF | Tetrahydrofuran |
| TosMIC | Toluenesulfonylmethyl isocyanide |
| $t_{1/2}$ | Half-life time |

EXAMPLES

The compounds of the present invention were prepared according to the following experimental procedures, using appropriate materials and conditions. The following examples are provided by way of illustration only but not to limit the scope of the present invention.
Preparation of Intermediates:

Intermediate-1a: 3-(4-Benzo[d]isothiazol-3-yl-piperazin-1-yl)-propan-1-ol

To a stirred suspension of 3-piperazin-1-yl-benzo[d]isothiazole (10 g, 45.6 mmol), $K_2CO_3$ (18.9 g, 137 mmol) and acetonitrile (100 mL) was added 1-bromo-3-propanol (19 g, 137 mmol) at RT. The reaction mixture was heated at 70-80° C. for 6 h. It was cooled to RT and poured onto water and maintained under stirring for 30 min during which solid was precipitated out. Solid was filtered, washed with n-hexane and dried under vacuum to obtain intermediate-1a. Yield: 10.13 g; $^1$H NMR (400 MHz, DMSO-$d_6$): δ 1.59-1.66 (m, 2H), 2.41-2.42 (m, 2H), 2.50-2.59 (m, 4H), 3.40-3.48 (m, 6H), 4.45 (bs, 1H), 7.41-7.45 (dd, J=7.6 Hz, 1H), 7.53-7.57 (dd, J=7.2 Hz, 1H), 8.03-8.06 (m, 2H); Mass (m/z): 278.1 $(M+H)^+$.

Intermediate-1b: 2-(4-Benzo[d]isothiazol-3-yl-piperazin-1-yl)-ethanol

Intermediate-1b was prepared by reacting 3-piperazin-1-yl-benzo[d]isothiazole with 2-bromo-ethanol following similar procedure as given in the preparation of intermediate-1a and some non-critical variations. Yield: 9.04 g; $^1$H NMR (400 MHz, DMSO-$d_6$): δ 2.67-2.69 (m, 4H), 2.72-2.76 (m, 2H), 3.43-3.45 (m, 4H), 3.72-3.75 (m, 2H) 4.48 (bs, 1H), 7.15-7.45 (dd, J=7.6 Hz, 1H), 7.53-7.57 (dd, J=7.6 Hz, 1H), 8.03-8.06 (m, 2H); Mass (m/z): 264.3 $(M+H)^+$.

Intermediate-1c: 3-[4-(3-Chloro-propyl)-piperazin-1-yl]-benzo[d]isothiazole

To a stirred suspension of 3-piperazin-1-yl-benzo[d]isothiazole (10 g, 45.6 mmol), KOH (7.6 g, 137 mmol) and THF:water (1:1, 100 mL) was added 1-bromo-3-chloro propane (19.6 g, 137 mmol) at RT and stirred at RT for 16 h. The resulted mixture was extracted with EtOAc (200 mL×3). The combined organic extracts were washed with brine (50 mL), dried over anhydrous $Na_2SO_4$, filtered and the solvent was evaporated under vacuum. The residue obtained was purified by column chromatography (silica gel, 15% EtOAc/petroleum ether) to obtain intermediate-1c. Yield: 9.68 g; $^1$H NMR (400 MHz, DMSO-$d_6$): δ 1.91-1.94 (m, 2H), 2.48-2.50 (m, 2H), 2.58-2.60 (m, 4H), 3.43-3.45 (m, 4H), 3.68-3.72 (m, 2H), 7.41-7.45 (dd, J=7.6 Hz, 1H), 7.53-7.57 (dd, J=7.2 Hz, 1H), 8.03-8.06 (m, 2H); Mass (m/z): 296.2 $(M+H)^+$.

Intermediate-1d: 3-[4-(6-Fluoro-benzo[d]isoxazol-3-yl)-piperidin-1-yl]-propan-1-ol Intermediate-1d was prepared from 6-fluoro-3-piperidin-4-yl-benzo[d]isoxazole following similar procedure as given in the preparation of intermediate-1a and some non-critical variations. Yield: 8.24 g; $^1$H NMR (400 MHz, DMSO-$d_6$): δ 1.78-1.83 (m, 2H), 2.00-2.03 (m, 2H), 2.21-2.27 (m, 2H), 2.68-2.71 (m, 1H), 2.98-3.01 (m, 2H), 3.11-3.17 (m, 2H), 3.69-3.73 (m, 2H), 4.53-4.62 (m, 2H), 4.48 (bs, 1H), 7.21-7.26 (m, 1H), 7.45-7.47 (m, 1H), 7.79 (s, 1H); Mass (m/z): 279.2 $(M+H)^+$.

Intermediate-1e: 3-[1-(3-Chloro-propyl)-piperidin-4-yl]-6-fluoro-benzo[d]isoxazole Intermediate-1e was prepared from 6-fluoro-3-piperidin-4-yl-benzo[d]isoxazole following similar procedure as given in the preparation of intermediate-1c and some non-critical variations. Yield: 7.9 g; $^1$H NMR (400 MHz, DMSO-$d_6$): δ 1.78-1.83 (m, 2H), 2.00-2.03 (m, 2H), 2.21-2.27 (m, 2H), 2.68-2.71 (m, 1H), 2.98-3.01 (m, 2H), 3.11-3.17 (m, 2H), 3.69-3.73 (m, 2H), 4.53-4.62 (m, 2H), 7.21-7.26 (m, 1H), 7.45-7.47 (m, 1H), 7.79 (s, 1H); Mass (m/z): 297.2, 299.2 (M+H)$^+$.

Intermediate-2a: 3-(2-Bromo-thiazol-4-yl)-5-methyl-[1,2,4]oxadiazole

Step-a: Sulfuric acid (14.27 g, 145.6 mmol) was added slowly to a stirred mixture of 2-bromo-thiazole-4-carboxylic acid (10.0 g, 48.5 mmol) and methanol (100 mL) at about 0° C. and stirred further at reflux temperature for 6 h. The reaction mixture was cooled to RT and poured onto water and maintained under stirring for 30 min during which solid was precipitated out. This solid was filtered, washed with water and dried in vacuum to obtain methyl 2-bromo-thiazole-4-carboxylate. Yield: 6.98 g; $^1$H NMR (400 MHz, DMSO-d$_6$): δ 3.89 (s, 3H), 8.55 (s, 1H); Mass (m/z): 223.1, 225.1 (M+H)$^+$.

Step-b: To a stirred mixture of methyl 2-bromo-thiazole-4-carboxylate (5.0 g, 22.5 mmol) and EtOAc (25 mL) was added NH$_4$OH (25 mL) at RT and stirred further for 3 h. The reaction mixture was extracted with EtOAc (100 mL×3). The combined organic extracts were washed with brine (50 mL), dried over anhydrous Na$_2$SO$_4$, filtered and the solvent was evaporated under vacuum to get 2-bromo-thiazole-4-carboxamide as solid. Yield: 3.60 g; Mass (m/z): 208.2, 210.2 (M+H)$^+$.

Step-c: To a stirred mixture of 2-bromo-thiazole-4-carboxamide (3.5 g, 17 mmol) and DMF (20 mL) was dropwise added POCl$_3$ (2.6 g, 17 mmol) and stirred at 60° C. for 1 h. The reaction mixture was poured onto water and neutralized with saturated NaHCO$_3$ solution. The mixture was extracted with EtOAc (100 mL×3) and combined organic extracts were washed with brine (50 mL), dried over anhydrous Na$_2$SO$_4$, filtered and the solvent was evaporated under vacuum. The residue was purified by column chromatography (silica gel, 15% EtOAc/petroleum ether) to get 2-bromo-thiazole-4-carbonitrile as solid. Yield: 2.2 g; $^1$H NMR (400 MHz, DMSO-d$_6$): δ 8.72 (s, 1H).

Step-d: To a stirred mixture of 2-bromo-thiazole-4-carbonitrile (2.0 g, 10.6 mmol), K$_2$CO$_3$ (2.95 g, 21.27 mmol) and ethanol (20 mL) was added hydroxylamine hydrochloride (1.5 g, 21.27 mmol) at RT and stirred at 80-85° C. for 4 h. The mixture was concentrated and diluted with water. The mixture was extracted with EtOAc (50 mL×3). The combined organic extracts were washed with brine (50 mL), dried over anhydrous Na$_2$SO$_4$, filtered and the solvent was evaporated under vacuum to get 2-bromo-N-hydroxy-thiazole-4-carboxamidine as solid which was used as such for the next step. Yield: 1.5 g.

Step-e: To a stirred mixture of 2-bromo-N-hydroxy-thiazole-4-carboxamidine (1.5 g, 6.8 mmol) and methanol (7.5 mL) was added triethyl orthoacetate (7.5 mL) at RT and stirred at 80° C. for 4 h. The mixture was concentrated to get oily mass. The crude residue was purified by column chromatography (silica gel, 15% EtOAc/petroleum ether) to obtain intermediate-2a as a solid. Yield: 1.06 g; $^1$H NMR (400 MHz, DMSO-d$_6$): δ 2.66 (s, 3H), 8.41 (s, 1H); Mass (m/z): 246.1, 248.1 (M+H)$^+$.

Intermediate-2b: 2-Chloro-5-(5-methyl-[1,2,4]oxadiazol-3-yl)-pyridine

6-Chloronicotinonitrile was reacted with hydroxylamine hydrochloride following a similar procedure as given in the preparation of step-d of intermediate-2a to obtain 6-chloro-N-hydroxy-nicotinamidine which was further treated with triethyl orthoacetate following a similar procedure as given in the preparation of step-e of intermediate-2a to obtain intermediate 2b. Yield: 2.40 g; Mass (m/z): 196.1, 198.1 (M+H)$^+$.

Intermediate-2c: 2-Chloro-6-(5-methyl-[1,2,4]oxadiazol-3-yl)-pyridine

6-Chloro-pyridine-2-carbonitrile was reacted with hydroxylamine hydrochloride following a similar procedure as given in the preparation of step-d of intermediate-2a to obtain 6-chloro-N-hydroxy-pyridine-2-carboxamidine which was further treated with triethyl orthoformate following a similar procedure as given in the preparation of step-e of intermediate-2a to obtain intermediate 2c. Yield: 2.60 g; Mass (m/z): 196.1, 198.1 (M+H)$^+$.

Intermediate-2d: 2-Chloro-5-(5-methyl-[1,2,4]oxadiazol-3-yl)-pyrazine

5-Chloro-pyrazine-2-carbonitrile was reacted with hydroxylamine hydrochloride following a similar procedure as given in the preparation of step-d of intermediate-2a to obtain 5-chloro-N-hydroxy-pyrazine-2-carboxamidine which was further treated with triethyl orthoformate following a similar procedure as given in the preparation of step-e of intermediate-2a to obtain intermediate 2d. Yield: 2.50 g; Mass (m/z): 197.1, 199.1 (M+H)$^+$.

Intermediate-2e: 5-(2-Bromo-thiazol-4-yl)-oxazole

To a stirred mixture of 2-bromo-thiazole-4-carbaldehyde (5 g, 26 mmol), K$_2$CO$_3$ (7.2 g, 52 mmol), and methanol (30 mL) portions were added TosMIC (10 g, 52 mmol) at RT and stirred at reflux temperature for 4 h. The mixture was concentrated, diluted with water and extracted with EtOAc (50 mL×3). The combined organic extracts were washed with brine (50 mL), dried over anhydrous Na$_2$SO$_4$, filtered and the solvent was evaporated under vacuum. The residue was purified by column chromatography (silica gel, 15% EtOAc/petroleum ether) to get intermediate-2e. Yield: 4.5 g; Mass (m/z): 231.2, 233.2 (M+H)$^+$.

Intermediate-2f: 2-Chloro-5-oxazol-5-yl-pyridine

6-Chloro-pyridine-3-carbaldehyde was reacted following a similar procedure as given in the preparation of intermediate-2e with some non-critical variations. Yield: 4.8 g; Mass (m/z): 181.3, 183.1 (M+H)$^+$.

Intermediate-2g: 2-(2-Bromo-thiazol-4-yl)-5-methyl-[1,3,4]oxadiazole

Step-a: To a mixture of 2-bromo-thiazole-4-carboxylic acid (5 g, 24.03 mmol) and 1,4-dioxane (20 mL) was added 1,1'-carbonyldiimidazole (4.67 g, 28.8 mmol) at RT and stirred for 30 min at 50° C. Then hydrazine hydrate (1.44 g, 28.84 mmol) was added at 50° C. and stirred at 50° C. for 1 h. The mixture was concentrated, diluted with water and extracted with EtOAc (100 mL×3). The combined organic extracts were washed with brine (50 mL), dried over anhydrous Na$_2$SO$_4$, filtered and the solvent was evaporated under vacuum. The residue was purified by column chromatography (silica gel, 30% EtOAc/petroleum ether) to get 2-bromo-thiazole-4-carboxylic acid hydrazide. Yield: 2.5 g; $^1$H NMR (400 MHz, CDCl$_3$): δ 4.06 (bs, 2H), 7.26 (bs, 1H), 7.90 (s, 1H); Mass (m/z): 222.0, 224.1 (M+H)$^+$.

Step-b: To a mixture 2-bromo-thiazole-4-carboxylic acid hydrazide (6.5 g, 29.27 mmol), acetic acid (7.9 g, 131.75 mmol) and toluene (35 mL) was added phosphorus oxychloride (6.7 g, 43.91 mmol) at RT and stirred at 100° C. for 2 h. The mixture was concentrated, diluted with water and neutralized with NH$_4$OH during which solids precipitated out. Then solids were filtered, washed with water and dried in vacuum to get intermediate-2g. Yield: 3 g; $^1$H NMR (400 MHz, CDCl$_3$): δ 2.62 (s, 3H), 8.10 (s, 1H); Mass (m/z): 246.1, 248.1 (M+H)$^+$.

Intermediate-2h: 2-(2-Bromo-thiazol-4-yl)-5-cyclopropyl-[1,3,4]oxadiazole

The compound of step-a of intermediate-2g was reacted with cyclopropyl carboxylic acid and phosphorus oxychloride in toluene following similar conditions as given in the preparation of step-b of intermediate-2g to obtain intermediate 2h. Yield: 3.0 g; Mass (m/z): 272.3, 274.3 (M+H)$^+$.

Intermediate-2i: 2-(2-Bromo-thiazol-5-yl)-5-methyl-[1,3,4]oxadiazole

2-Bromo-thiazole-5-carboxylic acid was reacted following a similar procedure as given in step-a of intermediate 2g to obtain 2-bromo-thiazole-5-carboxylic acid hydrazide which was further reacted following similar procedure as given in step-b of intermediate 2g to obtain intermediate-2i. Yield: 3.2 g; Mass (m/z): 246.2, 248.1 (M+H)$^+$.

Intermediate-2j: 5-(2-Bromo-thiazol-4-yl)-3-methyl-[1,2,4]oxadiazole

Step-a: To a mixture of acetonitrile (8 g, 95 mmol), sodium hydroxide (8.4 g, 218 mmol), ethanol (25 mL) and water (25 mL) was added hydroxylamine hydrochloride (14 g, 204 mmol) at RT and stirred at reflux temperature for 24 h. Reaction mixture was cooled to RT, concentrated under vacuum, diluted with ethanol and filtered. Filtrate was concentrated to get N-hydroxy-acetamidine. Yield: 2.2 g; Mass (m/z): 75.3 (M+H)$^+$.

Step-b: To a mixture of N-hydroxy-acetamidine (2.1 g 28 mmol), propylphosphonic anhydride solution (50 wt. % in ethyl acetate) (10.9 g 34 mmol), triethylamine (11.6 g 115 mmol) and EtOAc (20 mL) was added 2-bromo-thiazole-4-carboxylic acid (5 g, 23.9 mmol) at RT and stirred at reflux temperature for 8 h. Reaction mixture was cooled to RT, diluted with cold water and extracted with EtOAc (100 mL×3). The combined organic extracts were washed with brine (50 mL), dried over anhydrous Na$_2$SO$_4$, filtered and the solvent was evaporated under vacuum. The residue was purified by column chromatography (silica gel, 30% EtOAc/petroleum ether) to obtain intermediate-2j as solid. Yield: 1.0 g; Mass (m/z): 246.2, 248.2 (M+H)$^+$.

Intermediate-2k: 6-(3-Methyl-[1,2,4]oxadiazol-5-yl)-pyridin-2-ol

Intermediate-2k was prepared by reacting N-hydroxy-acetamidine obtained above with 6-hydroxy-pyridine-2-carboxylic acid following preparation step-b of intermediate-2j. Yield: 0.76 g; Mass (m/z): 178 (M+H)$^+$.

Intermediate-2l: 5-(3-Methyl-[1,2,4]oxadiazol-5-yl)-pyridin-2-ol

Intermediate-2l was prepared by reacting N-hydroxy-acetamidine obtained above with 6-hydroxy-nicotinic acid following preparation step-b of intermediate-2j. Yield: 0.5 g; Mass (m/z): 178.2 (M+H)$^+$.

Intermediate-2m: 6-(5-Methyl-[1,3,4]oxadiazol-2-yl)-pyridin-2-ol

To a mixture of 6-hydroxy-pyridine-2-carboxylic acid (2 g, 17 mmol), propylphosphonic anhydride solution (50 wt. % in ethyl acetate) (6.8 g, 21.44 mmol), triethylamine (7.2 g, 71.5 mmol) and EtOAc (10 mL) was added acetohydrazine (1.27 g, 14.3 mmol) at RT and stirred at reflux temperature for 8 h. Reaction mixture was cooled to RT, diluted with cold water and extracted with EtOAc (50 mL×3). The combined organic extracts were washed with brine (20 mL), dried over anhydrous Na$_2$SO$_4$, filtered and the solvent was evaporated under vacuum. The residue was purified by column chromatography (silica gel, 1.5% MeOH/DCM) to obtain intermediate-2m. Yield: 0.62 g; Mass (m/z): 178.2 (M+H)$^+$.

Example-1: 3-(4-{3-[4-(5-Methyl-[1,3,4]oxadiazol-2-yl)-thiazol-2-yloxy]-propyl}-piperazin-1-yl)-benzo[d]isothiazole

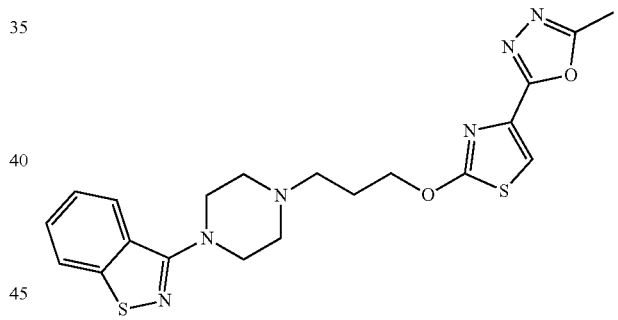

To a stirred suspension of 3-(4-benzo[d]isothiazol-3-yl-piperazin-1-yl)-propan-1-ol (5 g, 18 mmol, Intermediate-1a) in THF (25 mL), NaH (2.16 g, 90 mmol) was added at 0 to 10° C. to get a clear solution which was stirred further for 30 min at RT. 2-(2-bromo-thiazol-4-yl)-5-methyl-[1,3,4] oxadiazole (5.32 g, 21.6 mmol, intermediate-2g) was added to the reaction mixture at RT and heated at reflux temperature for 6 h. After cooling the reaction mixture poured onto water and extracted with EtOAc (100 mL×3). Combined organic extracts were washed with brine (50 mL), dried over anhydrous Na$_2$SO$_4$, filtered and the solvent was evaporated under vacuum. The residue was purified by column chromatography (silica gel, 2% MeOH/DCM) to get example-1. Yield: 2.84 g; H NMR (400 MHz, DMSO-d$_6$): δ 2.19-2.02 (m, 2H), 2.50 (s, 3H), 2.55-2.58 (m, 2H), 2.63 (m, 4H), 3.4 (m, 4H), 4.52-4.56 (m, 2H), 7.41-7.45 (m, 1H), 7.54-7.57 (m, 1H), 7.88 (s, 1H), 8.04-8.06 (m, 2H); Mass (m/z): 443.1 (M+H)$^+$.

Example-2: 3-(4-{3-[4-(5-Methyl-[1,3,4]oxadiazol-2-yl)-thiazol-2-yloxy]-propyl}-piperazin-1-yl)-benzo[d]isothiazole oxalate

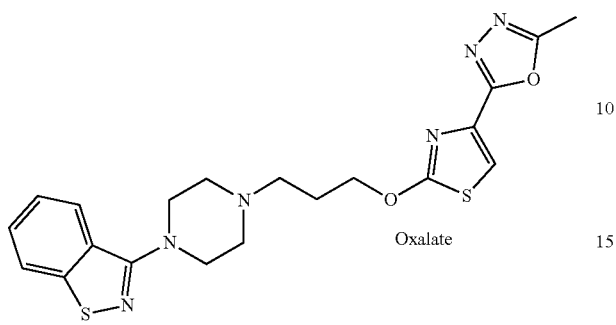

Oxalate

To a solution of example-1 (1 mmol) in methanol (20 mL), oxalic acid (1 mmol) was added. The mixture was stirred at 25° C. to 30° C. for 1 h, concentrated under vacuum to get solid. This solid was washed with diethyl ether and dried under vacuum to obtain example-2. ¹H NMR (400 MHz, CD₃OD): δ 2.35 (m, 2H), 2.62 (s, 3H), 3.33-3.50 (m, 6H), 3.78 (m, 4H), 4.69-4.72 (m, 2H), 7.46-7.50 (m, 1H), 7.56-7.60 (m, 1H), 7.78 (s, 1H), 7.96-7.98 (d, J=8 Hz, 1H), 8.06-8.08 (d, J=8 Hz, 1H); Mass (m/z): 443.1 (M+H)⁺.

Examples 3 to 34 were prepared following the procedure of Example-1 and Example-2 with some non-critical variations using suitable intermediates.

| Exp. No. | Chemical structure and IUPAC name | Characterization data |
|---|---|---|
| 3 | 3-(4-{2-[4-(5-Methyl-[1,3,4]oxadiazol-2-yl)-thiazol-2-yloxy]-ethyl}-piperazin-1-yl)-benzo[d]isothiazole | Yield: 6.0 g; ¹H NMR (400 MHz, DMSO-d₆): δ 2.57 (s, 3H), 2.72-2.73 (m, 4H), 2.85-2.86 (m, 2H), 3.41-3.45 (m, 4H), 4.62-4.60 (m, 2H), 7.42-7.46 (m, 1H), 7.54-7.58 (m, 1H), 7.90 (s, 1H), 8.05-8.07 (m, 2H); Mass (m/z): 429.1 (M + H)⁺. |
| 4 | Oxalate<br>3-(4-{2-[4-(5-Methyl-[1,3,4]oxadiazol-2-yl)-thiazol-2-yloxy]-ethyl}-piperazin-1-yl)-benzo[d]isothiazole oxalate | Yield: 5.80 g; ¹H NMR (400 MHz, CD₃OD): δ 2.62 (s, 3H), 3.49-3.51 (m, 2H), 3.73-3.84 (m, 8H), 5.01-5.02 (m, 2H), 7.47-7.51 (m, 1H), 7.57-7.61 (m, 1H), 7.86 (s, 1H), 7.97-7.99 (d, J = 8 Hz, 1H), 8.07-8.09 (d, J = 8 Hz, 1H); Mass (m/z): 429.1 (M + H)⁺. |
| 5 | 3-(4-{3-[4-(5-Cyclopropyl-[1,3,4]oxadiazol-2-yl)-thiazol-2-yloxy]-propyl}-piperazin-1-yl)-benzo[d]isothiazole | Yield: 0.4 g; ¹H NMR (400 MHz, DMSO-d₆): δ 1.17-1.23 (m, 4H), 2.26 (m, 1H), 2.35-2.37 (m, 2H), 2.63 (m, 4H), 3.29-3.31 (m, 2H), 3.45 (m, 4H), 4.52-4.55 (m, 2H), 7.41-7.45 (m, 1H), 7.53-7.57 (m, 1H), 7.86 (s,1H), 8.04-8.06 (m, 2H); Mass (m/z): 469.3 (M + H)⁺. |

| Exp. No. | Chemical structure and IUPAC name | Characterization data |
|---|---|---|
| 6 | 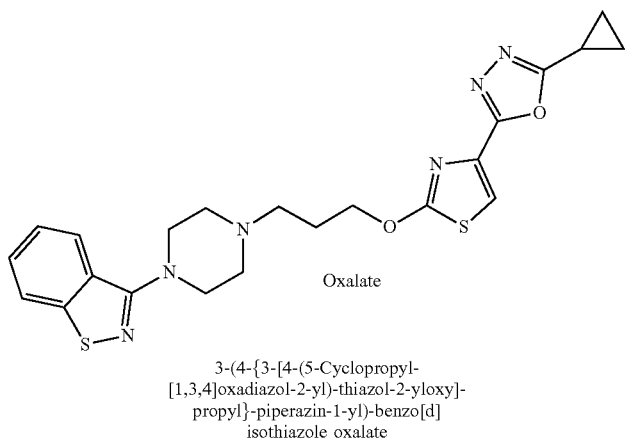

Oxalate 3-(4-{3-[4-(5-Cyclopropyl-[1,3,4]oxadiazol-2-yl)-thiazol-2-yloxy]-propyl}-piperazin-1-yl)-benzo[d]isothiazole oxalate | Yield: 0.5 g; $^1$H NMR (400 MHz, CD$_3$OD): δ 1.19-1.39 (m, 4H), 2.03-2.07 (m, 1H), 2.35-2.37 (m, 2H), 3.41-3.45 (m, 2H), 3.57 (m, 4H), 3.83 (m, 4H), 4.69-4.72 (m, 2H), 7.47-7.51 (m, 1H), 7.57-7.61 (m, 1H), 7.76 (s, 1H), 7.96-7.98 (d, J = 8 Hz, 1H), 8.08-8.06 (d, J = 8 Hz, 1H); Mass (m/z): 469.3 (M + H)$^+$. |
| 7 | 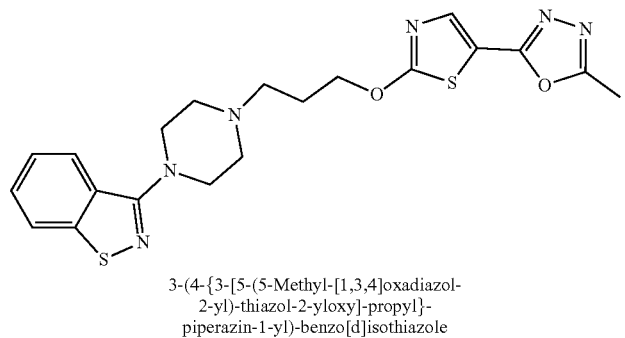

3-(4-{3-[5-(5-Methyl-[1,3,4]oxadiazol-2-yl)-thiazol-2-yloxy]-propyl}-piperazin-1-yl)-benzo[d]isothiazole | Yield: 0.5 g; $^1$H NMR (400 MHz, DMSO-d$_6$): δ 2.00-2.11 (m, 2H), 2.43 (s, 3H), 2.50-2.52 (m, 2H), 2.60 (m, 4H), 3.2 (m, 4H), 4.49-4.53 (m, 2H), 7.40-7.42 (m, 1H) 7.50-7.53 (m, 1H), 7.62 (s, 1H), 8.00-8.03 (m, 2H); Mass (m/z): 443.0 (M + H)$^+$. |
| 8 | 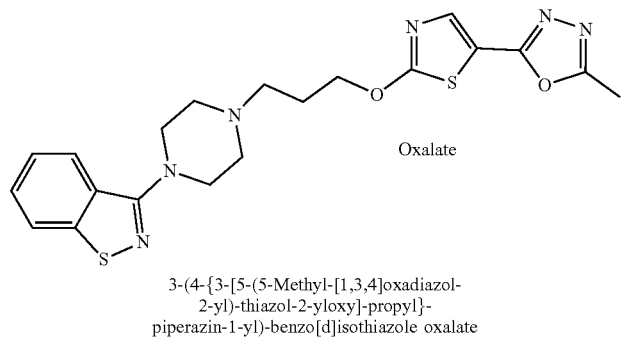

Oxalate 3-(4-{3-[5-(5-Methyl-[1,3,4]oxadiazol-2-yl)-thiazol-2-yloxy]-propyl}-piperazin-1-yl)-benzo[d]isothiazole oxalate | Yield: 0.5 g; $^1$H NMR (400 MHz, CD$_3$OD): δ 2.25 (m, 2H), 2.48 (s, 3H), 3.24-3.26 (m, 2H), 3.40 (m, 4H), 3.69 (m, 4H), 4.58 (m, 2H), 7.35-7.39 (m, 1H), 7.45-7.49 (m, 1H), 7.53 (s, 1H), 7.84-7.86 (d, J = 8.8 Hz, 1H), 7.94-7.96 (d, J = 8.4 Hz, 1H); Mass (m/z): 443.0 (M + H)$^+$. |
| 9 | 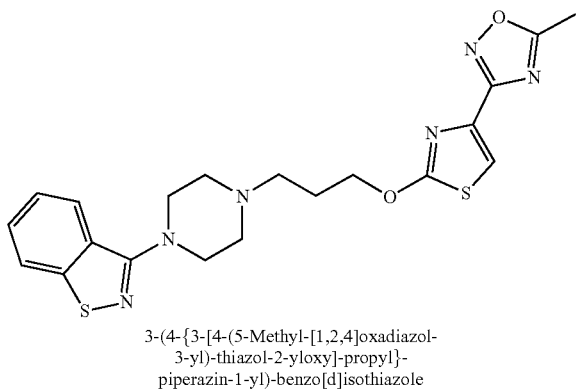

3-(4-{3-[4-(5-Methyl-[1,2,4]oxadiazol-3-yl)-thiazol-2-yloxy]-propyl}-piperazin-1-yl)-benzo[d]isothiazole | Yield: 0.42 g; $^1$H NMR (400 MHz, DMSO-d$_6$): δ 2.09-2.19 (m, 2H), 2.60 (s, 3H), 2.65-2.68 (m, 2H), 2.73 (m, 4H), 3.8 (m, 4H), 4.42-4.50 (m, 2H), 7.49-7.52 (m, 1H), 7.60-7.69 (m, 1H), 7.78 (s, 1H), 8.06-8.09 (m, 2H); Mass (m/z): 443.2 (M + H)$^+$. |

| Exp. No. | Chemical structure and IUPAC name | Characterization data |
|---|---|---|
| 10 | 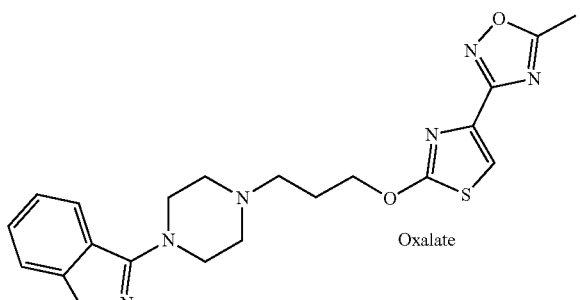<br>3-(4-{3-[4-(5-Methyl-[1,2,4]oxadiazol-3-yl)-thiazol-2-yloxy]-propyl}-piperazin-1-yl)-benzo[d]isothiazole oxalate | Yield: 0.48 g; $^1$H NMR (400 MHz, CD$_3$OD): δ 2.32-2.33 (m, 2H), 2.68 (s, 3H), 3.21-3.38 (m, 2H), 3.49-3.50 (m, 4H), 4.23-4.46 (m, 6H), 7.47-7.50 (dd, J = 7.6 Hz, 1H), 7.57-7.61 (dd, J = 7.2 Hz, 1H), 7.96-7.98 (d, J = 8.4 Hz, 1H), 8.07-8.09 (d, J = 8.4 Hz, 1H), 8.41 (s, 1H); Mass (m/z): 443.2 (M + H)$^+$. |
| 11 | 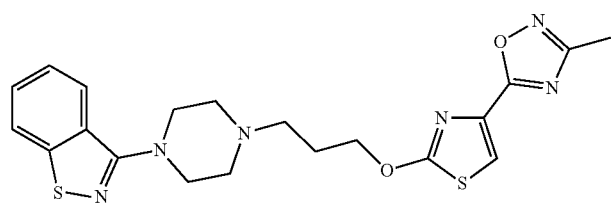 [SMILES: Cc1noc(-c2csc(OCCCN3CCN(c4nsc5ccccc45)CC3)n2)n1]<br>3-(4-{3-[4-(3-Methyl-[1,2,4]oxadiazol-5-yl)-thiazol-2-yloxy]-propyl}-piperazin-1-yl)-benzo[d]isothiazole | Yield: 0.35 g; $^1$H NMR (400 MHz, DMSO-d$_6$): δ 2.02-2.09 (m, 2H), 2.45 (s, 3H), 2.50-2.52 (m, 2H), 2.60 (m, 4H), 3.42 (m, 4H), 4.49-4.50 (m, 2H), 7.40-7.42 (m, 1H), 7.51-7.54 (m, 1H), 7.79 (s, 1H), 8.00-8.02 (m, 2H); Mass (m/z): 443.1 (M + H)$^+$. |
| 12 | 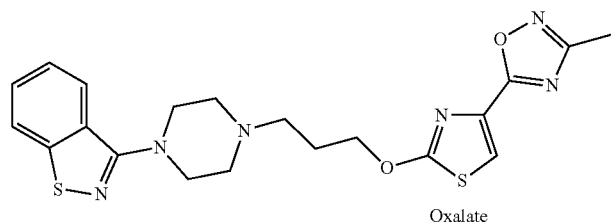 [SMILES: Cc1noc(-c2csc(OCCCN3CCN(c4nsc5ccccc45)CC3)n2)n1]<br>3-(4-{3-[4-(3-Methyl-[1,2,4]oxadiazol-5-yl)-thiazol-2-yloxy]-propyl}-piperazin-1-yl)-benzo[d]isothiazole oxalate | Yield: 0.37 g; $^1$H NMR (400 MHz, CD$_3$OD): δ 2.32 (s, 2H), 2.36 (s, 3H), 3.36-3.41 (m, 2H), 3.50 (m, 4H), 3.72 (m, 4H), 4.61 (m, 2H), 7.35-7.39 (m, 1H), 7.45-7.49 (m, 1H), 7.85-7.87 (m, 2H), 7.95-7.97 (d, J = 8 Hz, 1H); Mass (m/z): 443.2 (M + H)$^+$. |
| 13 | 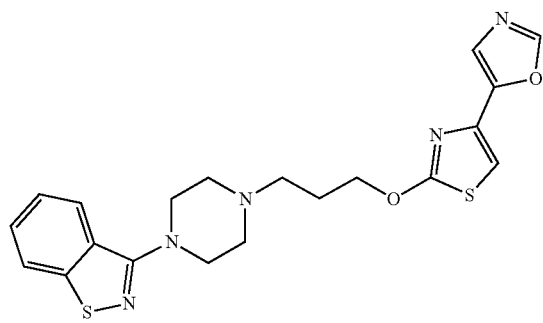 [SMILES: c1ccc2c(N3CCN(CCCOc4nc(-c5cnco5)cs4)CC3)nsc2c1]<br>3-{4-[3-(4-Oxazol-5-yl-thiazol-2-yloxy)-propyl]-piperazin-1-yl}-benzo[d]isothiazole | Yield: 0.25 g; $^1$H NMR (400 MHz, CD$_3$OD): δ 2.28 (m, 2H), 3.21 (m, 2H), 3.49 (m, 4H), 3.65-3.72 (m, 4H), 4.55-4.64 (m, 2H), 7.12 (s, 1H), 7.25 (s, 1H), 7.37 (m, 1H), 7.47 (m, 1H), 7.84-7.86 (m, 1H), 7.94 (m, 1H), 8.11 (s, 1H); Mass (m/z): 428.2 (M + H)$^+$. |

| Exp. No. | Chemical structure and IUPAC name | Characterization data |
|---|---|---|
| 14 | 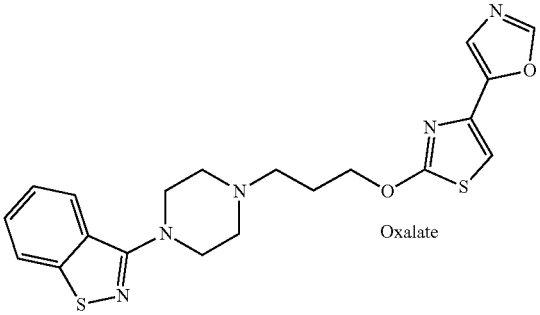 [SMILES: c1ccc2c(N3CCN(CCCOc4nc(-c5cnco5)cs4)CC3)nsc2c1]<br>3-{4-[3-(4-Oxazol-5-yl-thiazol-2-yloxy)-propyl]-piperazin-1-yl}-benzo[d]isothiazole oxalate | Yield: 0.27 g; $^1$H NMR (400 MHz, CD$_3$OD): δ 2.20-2.28 (m, 2H), 3.21-3.38 (m, 6H), 3.49-3.72 (m, 4H), 4.55-4.64 (m, 2H), 7.12 (s, 1H), 7.25 (s, 1H), 7.37-7.47 (m, 2H), 7.84-7.86 (dd, J = 8.0 Hz, 1H), 7.94 (m, 1H), 8.11 (s, 1H); Mass (m/z): 428.2 (M + H)$^+$. |
| 15 | 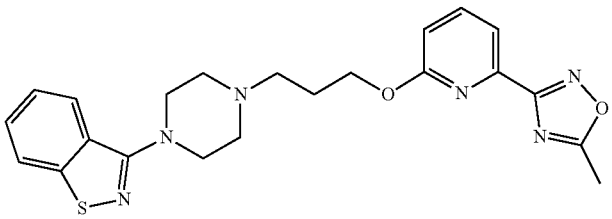 [SMILES: Cc1nc(-c2cccc(OCCCN3CCN(c4nsc5ccccc45)CC3)n2)no1]<br>3-(4-{3-[6-(5-Methyl-[1,2,4]oxadiazol-3-yl)-pyridin-2-yloxy]-propyl}-piperazin-1-yl)-benzo[d]isothiazole | Yield: 0.5 g; $^1$H NMR (400 MHz, DMSO-d$_6$): δ 2.18-2.20 (m, 2H), 2.50 (s, 3H), 3.19-3.22 (m, 2H), 3.50-3.55 (m, 6H), 4.39-4.45 (m, 4H), 6.80 (m, 1H), 7.26 (s, 1H), 7.35-7.40 (dd, J = 7.6 Hz, 1H), 7.53-7.60 (dd, J = 6.8 Hz, 1H), 7.66 (m, 1H), 7.80-7.85 (dd, J = 8 Hz, 1H), 7.90 (m, 1H); Mass (m/z): 437.0 (M + H)$^+$. |
| 16 | 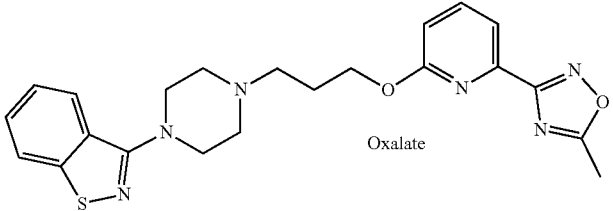 [SMILES: Cc1nc(-c2cccc(OCCCN3CCN(c4nsc5ccccc45)CC3)n2)no1]<br>3-(4-{3-[6-(5-Methyl-[1,2,4]oxadiazol-3-yl)-pyridin-2-yloxy]-propyl}-piperazin-1-yl)-benzo[d]isothiazole oxalate | Yield: 0.48 g; $^1$H NMR (400 MHz, CD$_3$OD): δ 2.20-2.28 (m, 2H), 2.58 (s, 3H), 3.21-3.38 (m, 2H), 3.62-3.65 (m, 6H), 4.42-4.48 (m, 4H), 6.88 (m, 1H), 7.36 (m, 1H), 7.45-7.47 (dd, J = 7.6 Hz, 1H), 7.63-7.65 (dd, J = 6.8 Hz, 1H), 7.76 (m, 1H), 7.84-7.86 (dd, J = 8 Hz, 1H), 7.94 (m, 1H); Mass (m/z): 437.0 (M + H)$^+$. |
| 17 | 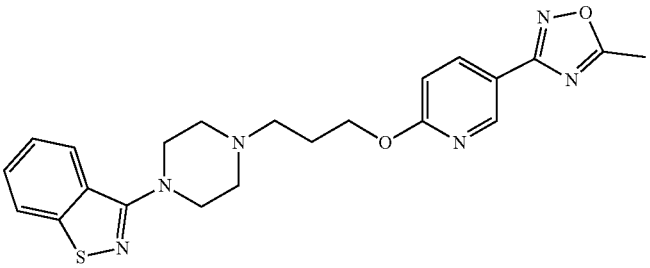 [SMILES: Cc1nc(-c2ccc(OCCCN3CCN(c4nsc5ccccc45)CC3)nc2)no1]<br>3-(4-{3-[5-(5-Methyl-[1,2,4]oxadiazol-3-yl)-pyridin-2-yloxy]-propyl}-piperazin-1-yl)-benzo[d]isothiazole | Yield: 0.21 g; $^1$H NMR (400 MHz, DMSO-d$_6$): δ 2.29-2.33 (m, 2H), 2.68 (s, 3H), 3.21-3.38 (m, 2H), 3.48-3.50 (m, 4H), 4.23-4.46 (m, 6H), 6.72-6.75 (m, 1H), 7.47-7.51 (dd, J = 7.6 Hz, 1H), 7.57-7.61 (dd, J = 7.2 Hz, 1H), 7.96-7.98 (d, J = 8.4 Hz, 1H), 8.03-8.05 (m, 2H), 8.49 (s, 1H); Mass (m/z): 437.0 (M + H)$^+$. |

| Exp. No. | Chemical structure and IUPAC name | Characterization data |
|---|---|---|
| 18 | 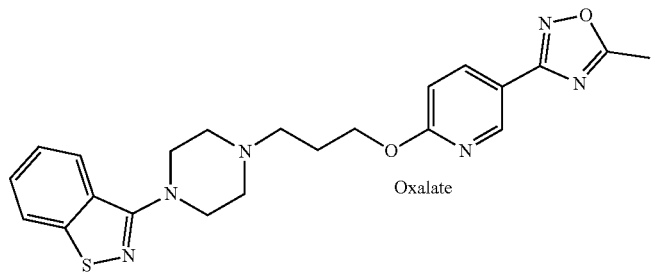 [SMILES: Cc1nc(-c2ccc(OCCCN3CCN(c4nsc5ccccc45)CC3)nc2)no1]<br>3-(4-{3-[5-(5-Methyl-[1,2,4]oxadiazol-3-yl)-pyridin-2-yloxy]-propyl}-piperazin-1-yl)-benzo[d]isothiazole oxalate | Yield: 0.51g; $^1$H NMR (400 MHz, CD3OD): δ 2.29-2.33 (m, 2H), 2.68 (s, 3H), 3.21-3.38 (m, 2H), 3.48-3.50 (m, 4H), 4.23-4.46 (m, 6H), 6.72-6.75 (m, 1H), 7.47-7.51 (dd, J = 7.6 Hz, 1H), 7.57-7.61 (dd, J = 7.2 Hz, 1H), 7.96-7.98 (d, J = 8.4 Hz, 1H), 8.03-8.05 (m, 2H), 8.49 (s, 1H); Mass (m/z): 437.0 (M + H)$^+$. |
| 19 | 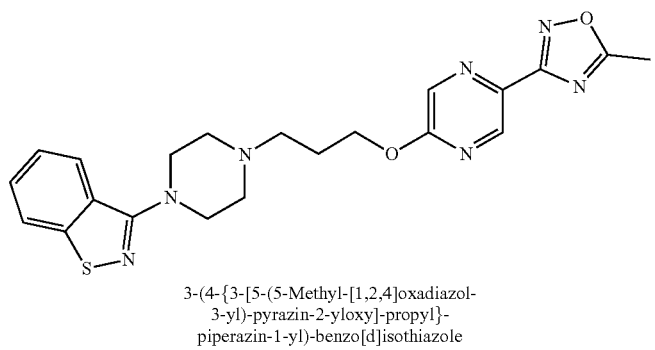<br>3-(4-{3-[5-(5-Methyl-[1,2,4]oxadiazol-3-yl)-pyrazin-2-yloxy]-propyl}-piperazin-1-yl)-benzo[d]isothiazole | Yield: 0.42 g; $^1$H NMR (400 MHz, CD$_3$OD): δ 2.37 (m, 2H), 2.71 (s, 3H), 3.32-3.48 (m, 2H), 3.58 (m, 4H), 3.83 (m, 4H), 4.61-4.63 (m, 2H), 7.47-7.51 (m, 1H), 7.57-7.61 (m, 1H), 7.97-7.99 (m, 1H), 8.07-8.09 (m, 1H), 8.39 (s, 1H), 8.89 (s, 1H): Mass (m/z): 438.1 (M + H)$^+$. |
| 20 | 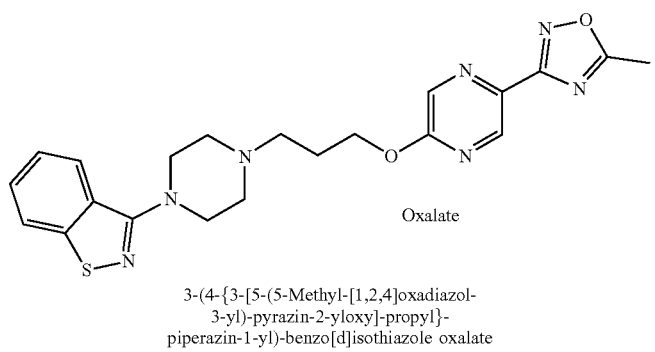<br>3-(4-{3-[5-(5-Methyl-[1,2,4]oxadiazol-3-yl)-pyrazin-2-yloxy]-propyl}-piperazin-1-yl)-benzo[d]isothiazole oxalate | Yield: 0.43 g; $^1$H NMR (400 MHz, CD$_3$OD): δ 2.37-2.38 (m, 2H), 2.71 (s, 3H), 3.47-3.50 (m, 2H), 3.58-3.83 (m, 8H), 4.61-4.63 (m, 2H), 7.47-7.51 (dd, J = 7.6 Hz, 1H), 7.57-7.61 (dd, J = 7.2 Hz, 1H), 7.77-7.99 (d, J = 8.0 Hz, 1H), 8.07-8.09 (d, J = 8.0 Hz, 1H), 8.39 (s, 1H), 8.89 (s, 1H): Mass (m/z): 438.0 (M + H)$^+$. |
| 21 | 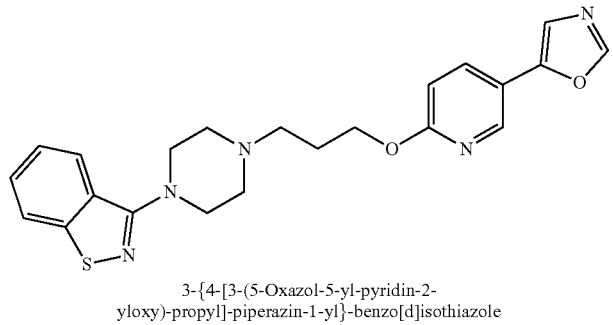<br>3-{4-[3-(5-Oxazol-5-yl-pyridin-2-yloxy)-propyl]-piperazin-1-yl}-benzo[d]isothiazole | Yield: 0.49 g; $^1$H NMR (400 MHz, DMSO-d$_6$): δ 2.29-2.32 (m, 2H), 3.39-3.42 (m, 4H), 3.58-3.62 (m, 4H), 4.49-4.52 (m, 4H), 6.89-6.90 (d, J = 8.8 Hz, 1H), 7.48-7.52 (m, 2H), 7.56-7.60 (dd, J = 7.6 Hz, 1H), 7.90-7.99 (d, J = 8.0 Hz, 1H), 8.05-8.09 (m, 2H), 8.31 (s, 1H), 8.59 (s, 1H); Mass (m/z): 422.0 (M + H)$^+$. |

-continued

| Exp. No. | Chemical structure and IUPAC name | Characterization data |
|---|---|---|
| 22 | 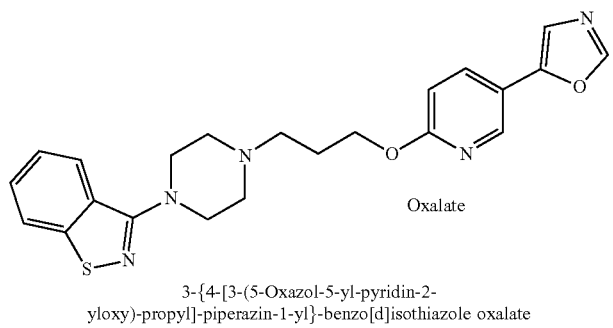

3-{4-[3-(5-Oxazol-5-yl-pyridin-2-yloxy)-propyl]-piperazin-1-yl}-benzo[d]isothiazole oxalate | Yield: 0.49 g; $^1$H NMR (400 MHz, CD$_3$OD): δ 2.34-2.37 (m, 2H), 3.48-3.52 (m, 4H), 3.61-3.63 (m, 4H), 4.51-4.54 (m, 4H), 6.95-6.98 (d, J = 8.8 Hz, 1H), 7.50-7.52 (m, 2H), 7.58-7.60 (dd, J = 7.6 Hz, 1H), 7.97-7.99 (d, J = 8.0 Hz, 1H), 8.05-8.09 (m, 2H), 8.28 (s, 1H), 8.56 (s, 1H); Mass (m/z): 422.0 (M + H)$^+$. |
| 23 | 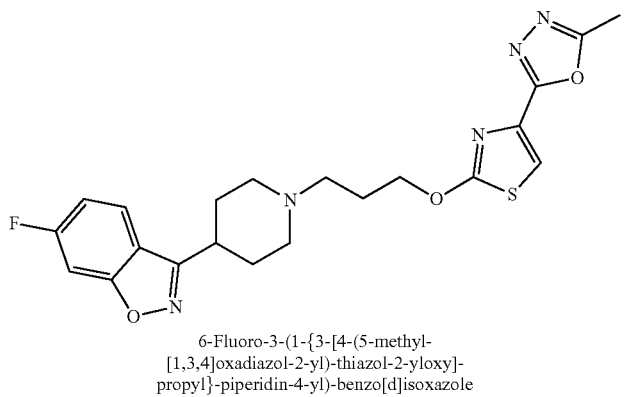

6-Fluoro-3-(1-{3-[4-(5-methyl-[1,3,4]oxadiazol-2-yl)-thiazol-2-yloxy]-propyl}-piperidin-4-yl)-benzo[d]isoxazole | Yield: 5.8 g; $^1$H NMR (400 MHz, DMSO-d$_6$): δ 2.01-2.32 (m, 7H), 2.66 (s, 3H), 3.00 (m, 4H), 3.16-3.17 (m, 2H), 4.54 (m, 2H), 7.27 (m, 1H), 7.69 (m, 1H), 7.89 (s, 1H), 8.01 (m, 1H); Mass (m/z): 444.3 (M + H)$^+$. |
| 24 | 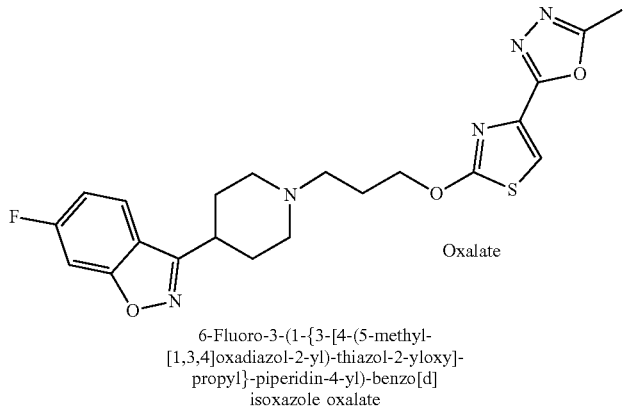

6-Fluoro-3-(1-{3-[4-(5-methyl-[1,3,4]oxadiazol-2-yl)-thiazol-2-yloxy]-propyl}-piperidin-4-yl)-benzo[d]isoxazole oxalate | Yield: 5.95 g; $^1$H NMR (400 MHz, CD$_3$OD): δ 2.26-2.49 (m, 7H), 2.62 (s, 3H), 3.33-3.34 (m, 2H), 3.35-3.78 (m, 4H), 4.69-4.72 (m, 2H), 7.21-7.26 (m, 1H), 7.45-7.47 (m, 1H), 7.79 (s, 1H), 7.90-7.92 (m, 1H); Mass (m/z): 444.1 (M + H)$^+$. |
| 25 | 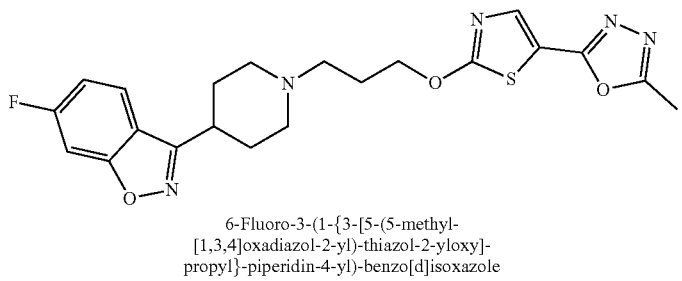

6-Fluoro-3-(1-{3-[5-(5-methyl-[1,3,4]oxadiazol-2-yl)-thiazol-2-yloxy]-propyl}-piperidin-4-yl)-benzo[d]isoxazole | Yield: 1.2 g; $^1$H NMR (400 MHz, CD$_3$OD): δ 2.02-2.05 (m, 5H), 2.17-2.20 (m, 2H), 2.48 (s, 3H), 2.52-2.56 (m, 2H), 3.02-3.10 (m, 4H), 4.50-4.53 (m, 2H), 7.04-7.09 (m, 1H), 7.27-7.30 (m, 1H), 7.73 (s, 1H), 7.79-7.82 (m, 1H); Mass (m/z): 444.0 (M + H)$^+$. |

| Exp. No. | Chemical structure and IUPAC name | Characterization data |
|---|---|---|
| 26 | 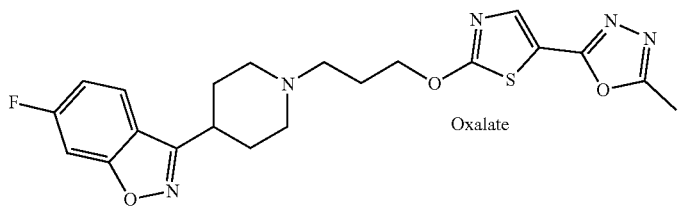 [SMILES: Cc1nnc(-c2cnc(OCCCN3CCC(c4noc5cc(F)ccc45)CC3)s2)o1]<br>6-Fluoro-3-(1-{3-[5-(5-methyl-[1,3,4]oxadiazol-2-yl)-thiazol-2-yloxy]-propyl}-piperidin-4-yl)-benzo[d]isoxazole oxalate | Yield: 1.3 g; $^1$H NMR (400 MHz, CD$_3$OD): δ 2.26-2.49 (m, 8H), 2.55 (s, 3H), 3.22 (m, 2H), 3.44 (m, 1H), 3.55-3.65 (m, 2H), 4.55-4.58 (m, 2H), 7.09-7.13 (m, 1H), 7.33-7.35 (m, 1H), 7.50 (s, 1H), 7.82-7.90 (m, 1H); Mass (m/z): 444.0 (M + H)$^+$. |
| 27 | 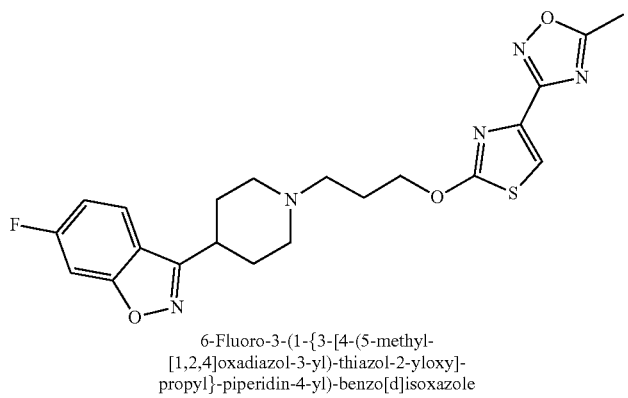<br>6-Fluoro-3-(1-{3-[4-(5-methyl-[1,2,4]oxadiazol-3-yl)-thiazol-2-yloxy]-propyl}-piperidin-4-yl)-benzo[d]isoxazole | Yield: 0.51 g; $^1$H NMR (400 MHz, CD$_3$OD): δ 1.78-1.83 (m, 2H), 2.00-2.03 (m, 2H), 2.21-2.27 (m, 2H), 2.63 (s, 3H), 2.68-2.71 (m, 2H), 2.92-3.01 (m, 2H), 3.11-3.17 (m, 1H), 3.69-3.73 (m, 2H), 4.53-4.62 (m, 2H), 7.27-7.29 (d, J = 8.0 Hz, 1H), 7.67-7.69 (d, J = 8.0 Hz, 1H), 8.02 (s, 1H), 8.41 (s, 1H); Mass (m/z): 444.1 (M + H)$^+$. |
| 28 | 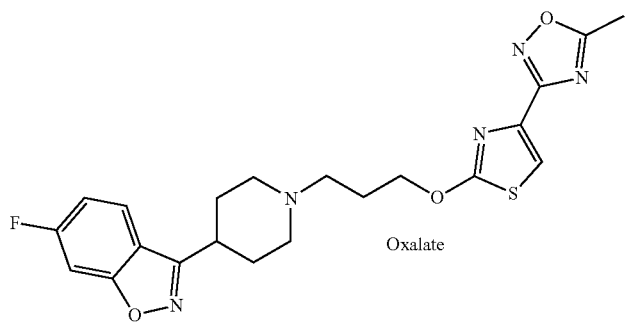 [SMILES: Cc1nc(-c2csc(OCCCN3CCC(c4noc5cc(F)ccc45)CC3)n2)no1]<br>6-Fluoro-3-(1-{3-[4-(5-methyl-[1,2,4]oxadiazol-3-yl)-thiazol-2-yloxy]-propyl}-piperidin-4-yl)-benzo[d]isoxazole oxalate | Yield: 0.51 g; $^1$H NMR (400 MHz, CD$_3$OD): δ 1.78-1.83 (m, 2H), 2.00-2.03 (m, 2H), 2.21-2.27 (m, 2H), 2.63 (s, 3H), 2.68-2.71 (m, 2H), 2.92-3.01 (m, 2H), 3.11-3.17 (m, 1H), 3.69-3.73 (m, 2H), 4.53-4.62 (m, 2H), 7.27-7.29 (d, J = 8.0 Hz, 1H), 7.67-7.69 (d, J = 8.0 Hz, 1H), 8.02 (s, 1H), 8.41 (s, 1H); Mass (m/z): 444.1 (M + H)$^+$. |
| 29 | 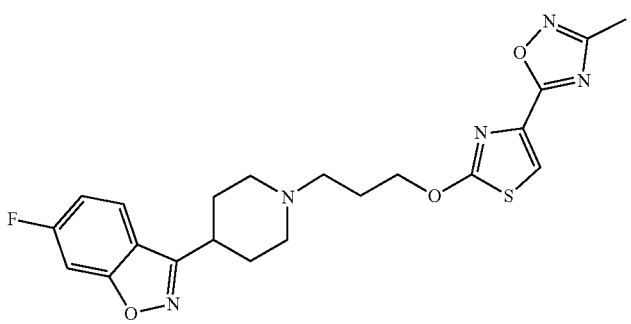 [SMILES: Cc1noc(-c2csc(OCCCN3CCC(c4noc5cc(F)ccc45)CC3)n2)n1]<br>6-Fluoro-3-(1-{3-[4-(3-methyl-[1,2,4]oxadiazol-5-yl)-thiazol-2-yloxy]-propyl}-piperidin-4-yl)-benzo[d]isoxazole | Yield: 0.7 g; $^1$H NMR (400 MHz, DMSO-d$_6$): δ 1.81-1.93 (m, 2H), 2.02-2.31 (m, 6H), 2.31 (m, 2H), 3.21 (m, 2H), 3.30-3.61 (m, 4H), 4.52 (m, 2H), 7.05-7.11 (m, 1H), 7.22-7.29 (m, 1H), 7.68 (m, 1H), 7.79 (s, 1H); Mass (m/z): 444.1 (M + H)$^+$. |

| Exp. No. | Chemical structure and IUPAC name | Characterization data |
|---|---|---|
| 30 | 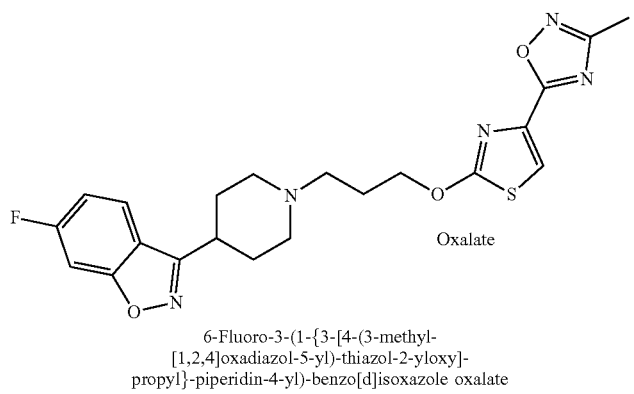<br>6-Fluoro-3-(1-{3-[4-(3-methyl-[1,2,4]oxadiazol-5-yl)-thiazol-2-yloxy]-propyl}-piperidin-4-yl)-benzo[d]isoxazole oxalate | Yield: 0.72 g; $^1$H NMR (400 MHz, CD$_3$OD): δ 2.03-2.35 (m, 8H), 2.36 (m, 2H), 3.32 (m, 2H), 3.34-3.72 (m, 4H), 4.60 (m, 2H), 7.10-7.14 (m, 1H), 7.33-7.35 (d, J = 8 Hz, 1H), 7.80 (m, 1H), 7.88 (s, 1H); Mass (m/z): 444.1 (M + H)$^+$. |
| 31 | 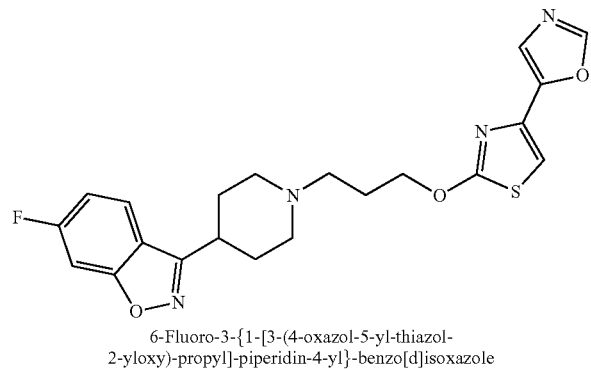<br>6-Fluoro-3-{1-[3-(4-oxazol-5-yl-thiazol-2-yloxy)-propyl]-piperidin-4-yl}-benzo[d]isoxazole | Yield: 0.5 g; $^1$H NMR (400 MHz, DMSO-d$_6$): δ 1.68-1.73 (m, 2H), 2.05-2.09 (m, 2H), 2.20-2.29 (m, 2H), 2.60-2.69 (m, 2H), 2.82-3.01 (m, 2H), 3.01-3.10 (m, 1H), 3.54-3.63 (m, 2H), 4.49-4.52 (m, 2H), 7.10 (s, 1H), 7.20 (s, 1H), 7.20-7.29 (d, J = 8.0 Hz, 1H), 7.60-7.69 (d, J = 8.0 Hz, 1H) 8.00 (s, 1H), 8.09 (s, 1H); Mass (m/z): 428.1 (M + H)$^+$. |
| 32 | 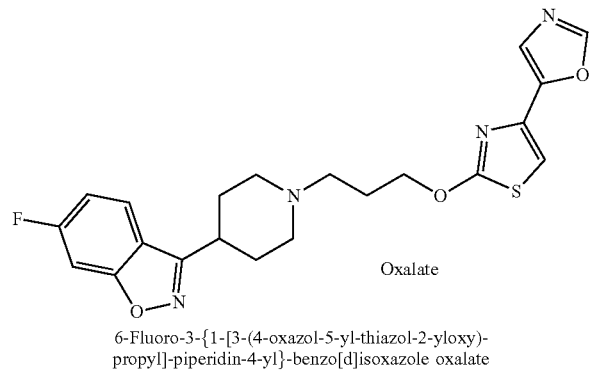<br>6-Fluoro-3-{1-[3-(4-oxazol-5-yl-thiazol-2-yloxy)-propyl]-piperidin-4-yl}-benzo[d]isoxazole oxalate | Yield: 0.5 g; $^1$H NMR (400 MHz, CD$_3$OD): δ 1.78-1.83 (m, 2H), 2.00-2.03 (m, 2H), 2.21-2.27 (m, 2H), 2.68-2.71 (m, 2H), 2.98-3.01 (m, 2H), 3.11-3.17 (m, 1H), 3.69-3.73 (m, 2H), 4.53-4.62 (m, 2H), 7.12 (s, 1H), 7.25 (s, 1H), 7.27-7.29 (d, J = 8.0 Hz, 1H), 7.67-7.69 (d, J = 8.0 Hz, 1H), 8.02 (s, 1H), 8.11 (s, 1H); Mass (m/z): 428.3 (M + H)$^+$. |
| 33 | 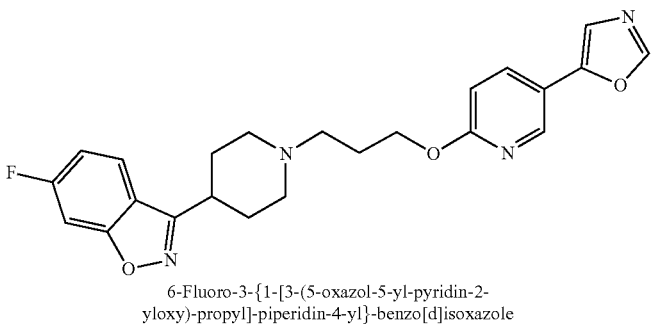<br>6-Fluoro-3-{1-[3-(5-oxazol-5-yl-pyridin-2-yloxy)-propyl]-piperidin-4-yl}-benzo[d]isoxazole | Yield: 0.52 g; $^1$H NMR (400 MHz, DMSO-d$_6$): δ 1.66-1.73 (m, 2H), 2.09-2.13 (m, 2H), 2.29-2.37 (m, 2H), 2.61-2.69 (m, 2H), 2.92-3.00 (m, 2H), 3.11-3.19 (m, 1H), 3.60-3.71 (m, 2H), 4.52-4.60 (m, 2H), 6.90 (s, 1H), 7.19-7.20 (m, 1H), 7.40-7.49 (m, 2H), 7.86-7.90 (m, 1H), 8.02 (s, 1H), 8.25 (s, 1H), 8.50 (s, 1H); Mass (m/z): 423.0 (M + H)$^+$. |

| Exp. No. | Chemical structure and IUPAC name | Characterization data |
|---|---|---|
| 34 | 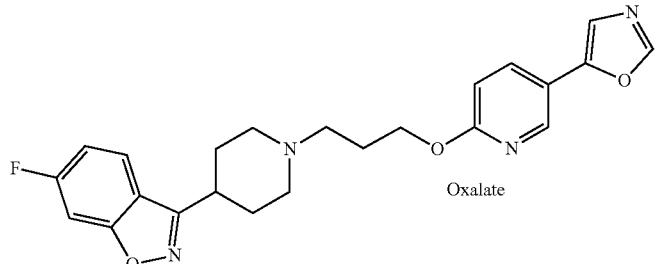

6-Fluoro-3-{1-[3-(5-oxazol-5-yl-pyridin-2-yloxy)-propyl]-piperidin-4-yl}-benzo[d]isoxazole oxalate | Yield: 0.54 g; $^1$H NMR (400 MHz, CD$_3$OD): δ 1.78-1.83 (m, 2H), 2.00-2.03 (m, 2H), 2.21-2.27 (m, 2H), 2.68-2.71 (m, 2H), 2.97-3.01 (m, 2H), 3.11-3.17 (m, 1H), 3.69-3.73 (m, 2H), 4.53-4.62 (m, 2H), 6.96 (s, 1H), 7.21-7.24 (m, 1H), 7.45-7.52 (m, 2H), 7.90-7.91 (m, 1H), 8.06 (s, 1H), 8.28 (s, 1H), 8.56 (s, 1H); Mass (m/z): 423.0 (M + H)$^+$. |

Example-35: 3-(4-{3-[6-(5-Methyl-[1,3,4]oxadiazol-2-yl)-pyridin-2-yloxy]-propyl}-piperazin-1-yl)-benzo[d]isothiazole

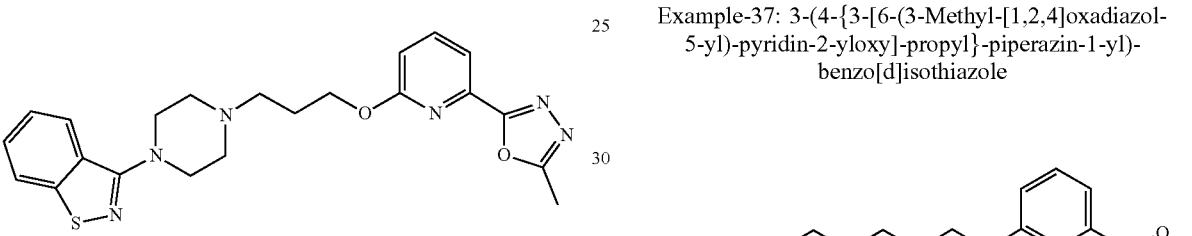

To a mixture of intermediate-2m (2 g, 11.28 mmol) and acetonitrile (20 mL) was added K$_2$CO$_3$ (4.67 g, 33.8 mmol) and intermediate-1c (4 g, 13.56 mmol) were added at RT; and stirred for 6 h at reflux temperature. Reaction mixture poured onto water, the mixture was extracted with EtOAc (50 mL×3). Combined organic extracts were washed with brine (25 mL), dried over anhydrous Na$_2$SO$_4$, filtered and evaporated. The residue was purified by column chromatography (silica gel 400 MeOH/DCM) to get titled compound. Yield: 1.2 g; $^1$H NMR (400 MHz, DMSO-d$_6$): δ 2.25 (m, 2H), 2.45 (s, 3H), 3.40 (m, 2H), 3.50 (m, 4H), 3.77 (m, 4H), 4.52 (m, 2H), 7.08-7.11 (d, J=8 Hz, 1H), 7.39-7.41 (m, 1H), 7.51-7.59 (m, 1H), 7.81-7.94 (m, 3H), 8.00 (d, J=8 Hz, 1H); Mass (m/z): 437.2 (M+H)$^+$.

Example-36: 3-(4-{3-[6-(5-Methyl-[1,3,4]oxadiazol-2-yl)-pyridin-2-yloxy]-propyl}-piperazin-1-yl)-benzo[d]isothiazole oxalate

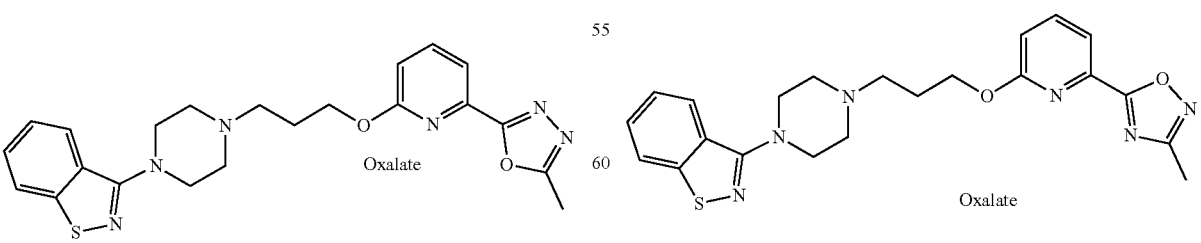

Example-35 was converted to example-36 using a similar procedure as given in the preparation of example-2. Yield: 1.3 g; $^1$H NMR (400 MHz, CD$_3$OD): δ 2.36 (m, 2H), 2.48 (s, 3H), 3.44 (m, 2H), 3.57 (m, 4H), 3.83 (m, 4H), 4.63 (m, 2H), 7.10-7.12 (d, J=8 Hz, 1H), 7.47-7.51 (m, 1H), 7.57-7.61 (m, 1H), 7.88-7.98 (m, 3H), 8.09 (d, J=8 Hz, 1H); Mass (m/z): 437.2 (M+H)$^+$.

Example-37: 3-(4-{3-[6-(3-Methyl-[1,2,4]oxadiazol-5-yl)-pyridin-2-yloxy]-propyl}-piperazin-1-yl)-benzo[d]isothiazole Example-37 was prepared by reacting intermediate-1c and intermediate-2k using a similar procedure as given in the preparation of example-35. Yield: 1.2 g; $^1$H NMR (400 MHz, DMSO-d$_6$): δ 2.25 (m, 2H), 2.45 (s, 3H), 3.40 (m, 2H), 3.51 (m, 4H), 3.80 (m, 4H), 4.59 (m, 2H), 7.05-7.10 (d, J=8 Hz, 1H), 7.41-7.50 (m, 1H), 7.50-7.59 (m, 1H), 7.80-7.92 (m, 3H), 8.02 (d, J=8 Hz, 1H); Mass (m/z): 437.2 (M+H)$^+$.

Example-38: 3-(4-{3-[6-(3-Methyl-[1,2,4]oxadiazol-5-yl)-pyridin-2-yloxy]-propyl}-piperazin-1-yl)-benzo[d]isothiazole oxalate Example-37 was converted to example-38 using a similar procedure as given in the preparation of example-2. Yield: 1.2 g; $^1$H NMR (400 MHz, CD$_3$OD): δ 2.36 (m, 2H), 2.48 (s, 3H), 3.44 (m, 2H), 3.57 (m, 4H), 3.83 (m, 4H), 4.63 (m, 2H), 7.10-7.12 (d, J=8 Hz, 1H), 7.47-7.51 (m, 1H), 7.57-7.61 (m, 1H), 7.88-7.98 (m, 3H), 8.09 (d, J=8 Hz, 1H); Mass (m/z): 437.2 (M+H)⁺.

Example-39: 3-{4-[3-(4-[1,2,4]oxadiazol-3-yl-thiazol-2-yloxy)-propyl]-piperazin-1-yl}-benzo[d]isothiazole

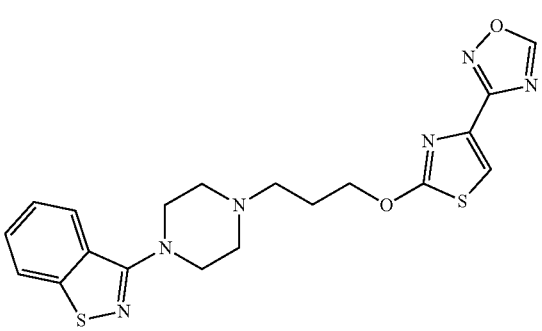 [SMILES: c1ccc2c(N3CCN(CCCOc4nc(-c5ncon5)cs4)CC3)nsc2c1]

Step-a: To a stirred suspension of intermediate-1a (1 g, 3.6 mmol) and THF (10 mL), NaH was added (0.17 g, 7.2 mmol) at 0° C. followed by 2-bromo-thiazole-4-carbonitrile (0.8 g, 5.4 mmol) at 0° C. Reaction mixture was brought to RT and stirred at reflux temperature for 6 h. Reaction mixture was poured onto water and extracted with EtOAc (100 mL×3). Combined organic extracts were washed with brine (50 mL), dried over anhydrous Na₂SO₄, filtered and the solvent was evaporated under vacuum. The residue was purified by column chromatography (silica gel 2% methanol in dichloromethane) to obtain 2-[3-(4-benzo[d]isothiazol-3-yl-piperazin-1-yl)-propoxy]-thiazole-4-carbonitrile. Yield: 1.05 g; Mass (m/z): 386.1 (M+H)⁺.

Step-b: To a mixture of 2-[3-(4-benzo[d]isothiazol-3-yl-piperazin-1-yl)-propoxy]-thiazole-4-carbonitrile (1 g, 2.6 mmol), K₂CO₃ (0.71 g, 5.2 mmol) and ethanol (10 mL), hydroxylamine hydrochloride (0.36 g, 5.2 mmol) was added at RT. Reaction mixture was stirred at reflux for 4 h, cooled to RT and evaporated under vacuum. The residue thus obtained was poured onto water and extracted with EtOAc (100 mL×3). Combined organic extracts were washed with brine (50 mL), dried over anhydrous Na₂SO₄, filtered and the solvent was evaporated under vacuum. The residue was purified by column chromatography (silica gel 2% methanol in dichloromethane) to obtain 2-[3-(4-benzo[d]isothiazol-3-yl-piperazin-1-yl)-propoxy]-N-hydroxy-thiazole-4-carboxamidine and proceeded to the next step without further purification. Yield: 0.79.

Step-c: To a mixture of 2-[3-(4-benzo[d]isothiazol-3-yl-piperazin-1-yl)-propoxy]-N-hydroxy-thiazole-4-carboxamidine (0.7 g, 1.6 mmol) and methanol (7 mL) was added triethyl orthoformate (7 mL) at RT and stirred at reflux temperature for 4 h and evaporated. The residue was purified by column chromatography (1% methanol in chloroform) to get example-39. Yield: 0.5 g; ¹H NMR (400 MHz, DMSO-d₆): δ 2.00-2.31 (m, 2H), 3.29-3.56 (m, 2H), 3.55-3.62 (m, 4H), 3.77-3.80 (m, 4H) 4.65-4.70 (m, 2H), 7.40-7.49 (dd, J=7.6 Hz, 1H), 7.50-7.59 (dd, J=7.2 Hz, 1H), 7.78 (s, 1H), 7.90-7.92 (d, J=8.0 Hz, 1H), 8.00-8.01 (d, J=8.0 Hz, 1H), 9.26 (s, 1H); Mass (m/z): 428.9 (M+H)⁺.

Example-40: 3-{4-[3-(4-[1,2,4]oxadiazol-3-yl-thiazol-2-yloxy)-propyl]-piperazin-1-yl}-benzo[d]isothiazole oxalate

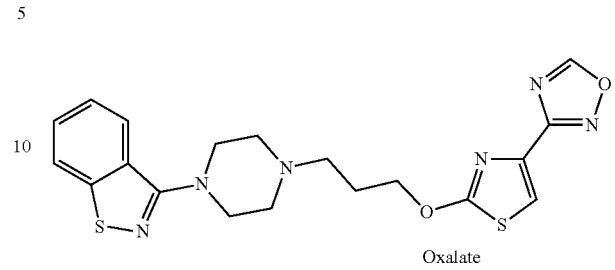

Example-39 was converted to example-40 using a similar procedure as given in the preparation of example-2. Yield: 0.5 g; ¹H NMR (400 MHz, CD₃OD): δ 2.12-2.42 (m, 2H), 3.32-3.62 (m, 2H), 3.63-3.70 (m, 4H), 3.85-3.89 (m, 4H) 4.70-4.71 (m, 2H), 7.47-7.51 (dd, J=7.6 Hz, 1H), 7.57-7.61 (dd, J=7.2 Hz, 1H), 7.80 (s, 1H), 7.96-7.98 (d, J=8.0 Hz, 1H), 8.07-8.09 (d, J=8.0 Hz, 1H), 9.30 (s, 1H); Mass (m/z): 428.9 (M+H)⁺.

Example-41: 3-{4-[3-(6-[1,2,4]Oxadiazol-3-yl-pyridin-2-yloxy)-propyl]-piperazin-1-yl}-benzo[d]isothiazole

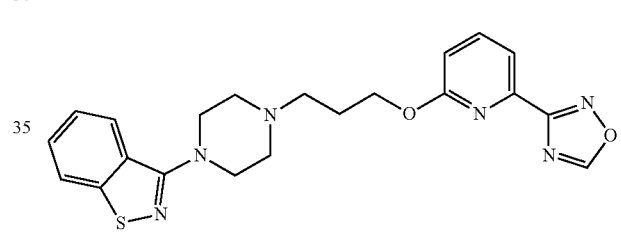

Example-41 was prepared by reacting intermediate-1a and 6-chloropyridine-2-carbonitrile using a similar procedure as given in the preparation of example-39. Yield: 0.28 g; ¹H NMR (400 MHz, DMSO-d₆): δ 2.20 (m, 2H), 3.35 (m, 2H), 3.41 (m, 4H), 3.70 (m, 4H), 4.45 (m, 2H), 7.08-7.10 (d, J=8 Hz, 1H), 7.41-7.43 (m, 1H), 7.55-7.59 (m, 1H), 7.85-7.96 (m, 3H), 8.00 (d, J=8 Hz, 1H), 9.05 (s, 1H); Mass (m/z): 423.0 (M+H)⁺.

Example-42: 3-{4-[3-(6-[1,2,4]Oxadiazol-3-yl-pyridin-2-yloxy)-propyl]-piperazin-1-yl}-benzo[d]isothiazole oxalate

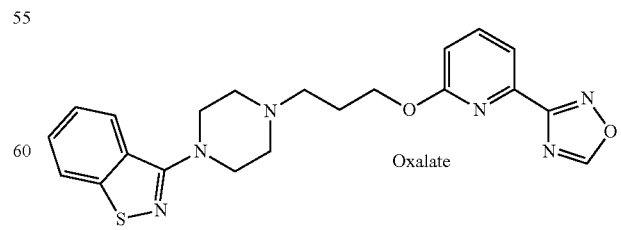

Example-41 was converted to example-42 using a similar procedure as given in the preparation of example-2. Yield: 0.3 g; ¹H NMR (400 MHz, CD₃OD): δ 2.29-2.33 (m, 2H), 3.32-3.36 (m, 4H), 3.48-3.50 (m, 6H), 4.23-4.26 (m, 2H), 6.72-6.75 (m, 1H), 7.47-7.51 (dd, J=8.0 Hz, 1H), 7.57-7.61 (dd, J=7.6 Hz, 1H), 7.96-7.98 (d, J=8.0 Hz, 1H), 8.05-8.07 (d, J=8.0 Hz, 1H), 8.13-8.16 (m, 1H), 8.49-8.50 (m, 1H), 9.30 (s, 1H); Mass (m/z): 423.0 (M+H)$^+$.

Example-43: Determination of $K_i$ Values at 5-HT$_{1A}$ Receptor

Materials and Method

Receptor source: Recombinant mammalian cells (HEK293-EBNA)
Radioligand: [$^3$H]-8-Hydroxy DPAT (200 Ci/mmol)
Final ligand concentration: 0.8 nM
Non-specific determinant: 0.1 mM U92016A
Reference compound: U92016A
Positive control: U92016A
Incubation conditions: Reactions were carried out in buffer with pH 7.4 containing 50 mM Tris-HCl, 0.5 mM EDTA, 10 mM MgSO$_4$, 0.1% Ascorbic acid for 2 h at RT. The reaction was terminated by rapid vacuum filtration onto the glass fiber filters. Radioactivity trapped onto the filters was determined and compared to the control values in order to ascertain any interactions of the test compound(s) with cloned human 5-HT$_{1A}$ receptor binding site.

Example-44: Determination of $K_i$ Values at 5-HT$_{2A}$ Receptor

Materials and Method

Receptor source: Recombinant mammalian cells (CHO-K1)
Radioligand: [$^3$H]-Ketanserine (41.9 Ci/mmol)
Final ligand concentration: 1.25 nM
Non-specific determinant: 0.1 mM 1-Napthyl piperazine (1-NP)
Reference compound: 1-Napthyl piperazine (1-NP)
Positive control: 1-Napthyl piperazine (1-NP)
Incubation conditions: Reactions were carried out in buffer with pH 7.4 containing 50 mM Tris-HCl, 4 mM CaCl$_2$, 0.1% Ascorbic acid for 1 h at RT. The reaction was terminated by rapid vacuum filtration onto the glass fiber filters. Radioactivity trapped onto the filters was determined and compared to the control values in order to ascertain any interactions of the test compound(s) with cloned human 5-HT$_{2A}$ receptor binding site.

Example-45: Determination of $K_i$ Values at D$_{2S}$ Receptor

Materials and Method

Receptor source: Recombinant mammalian cells (CHO-K1)
Radioligand: [$^3$H]-Raclopride (80.8 Ci/mmol)
Final ligand concentration: 4 nM
Non-specific determinant: 0.1 mM Haloperidol
Reference compound: Haloperidol
Positive control: Haloperidol
Incubation conditions: Reactions were carried out in buffer with pH 7.4 containing 50 mM Tris-HCl, 120 mM NaCl, 5 mM KCl, 5 mM MgCl$_2$, 1 mM EDTA for 2 h at RT. The reaction was terminated by rapid vacuum filtration onto the glass fiber filters. Radioactivity trapped onto the filters was determined and compared to the control values in order to ascertain any interactions of the test compound(s) with cloned human dopamine D$_2$s receptor binding site.

Example-46: Determination of $K_i$ Values at SERT Receptor

Materials and Method

Receptor source: Recombinant mammalian cells (HEK293)
Radioligand: [$^3$H]-Citalopram (80.8 Ci/mmol)
Final ligand concentration: 2 nM
Non-specific determinant: 0.1 mM Venlafaxine
Reference compound: Venlafaxine
Positive control: Venlafaxine
Incubation conditions: Reactions were carried out in buffer with pH 7.4 containing 50 mM Tris-HCl, 150 mM NaCl, 5 mM KCl and Scintillation proximity assay (SPA) beads (0.1 mg/well) for 3 h at RT. Radioactivity proximal to SPA beads was determined by scintillation proximity assay and compared to the control values in order to ascertain any interactions of the test compound(s) with cloned human SERT receptor binding site.

Example-47: Determination of $K_i$ Values at Adrenergic $\alpha_{1B}$ Receptor

Materials and Method

Receptor source: Recombinant mammalian cells (Chem-1)
Radioligand: [$^3$H]-Prazosin (77.4 Ci/mmol)
Final ligand concentration: 1 nM
Non-specific determinant: 0.1 mM Prazosin
Reference compound: Prazosin
Positive control: Prazosin
Incubation conditions: Reactions were carried out in buffer with pH 7.4 containing 67 mM Tris-HCl, 67 µM EDTA, 13 mM EDTA for 1 h at RT. The reaction was terminated by rapid vacuum filtration onto the glass fiber filters. Radioactivity trapped onto the filters was determined and compared to the control values in order to ascertain any interactions of the test compound(s) with cloned human adrenergic $\alpha_{1B}$ receptor binding site.

Example-48: Determination of $K_i$ values at Histamine H$_1$ receptor

Materials and Method

Receptor source: Recombinant mammalian cells (CHO-K1)
Radioligand: [$^3$H]-Pyrilamine (20.7 Ci/mmol)
Final ligand concentration: 2 nM
Non-specific determinant: 0.1 mM Pyrilamine
Reference compound: Pyrilamine
Positive control: Pyrilamine
Incubation conditions: Reactions were carried out in buffer with pH 7.4 containing 67 mM Tris-HCl and SPA beads (0.1 mg/well) for 1 h at 37° C. Radioactivity proximal to SPA beads was determined by scintillation proximity assay and compared to the control values in order to ascertain any interactions of the test compound(s) with cloned human histamine H$_1$ receptor binding site.

TABLE 1

Ki values of the test compounds at
h5-HT$_{1A}$, h5-HT$_{2A}$, hD$_2$, hSERT, hα$_{1B}$, and hH$_1$.

| Example No. | 5-HT$_{1A}$ (nM) | 5-HT$_{2A}$ (nM) | D$_2$ (nM) | SERT (nM) | Alpha$_{1B}$ (nM) | H$_1$ (nM) |
|---|---|---|---|---|---|---|
| 1 | 0.10 | 0.35 | 0.51 | 54.3 | 12.5 | 8.8 |
| 2 | 0.15 | 0.24 | 0.41 | 80.0 | 13.3 | 9.9 |
| 10 | 0.4 | 0.5 | 1.5 | 217.2 | 44.1 | 4.2 |
| 12 | 0.2 | 0.5 | 0.4 | 157.3 | 14.4 | 4.1 |
| 22 | 0.3 | 0.01 | 0.4 | 18.8 | 5.7 | 1.8 |
| 24 | 1.8 | 0.3 | 0.7 | 1665.6 | 1.5 | 3.5 |

Example-49: Rodent Pharmacokinetic Study

Male Wistar rats (250±50 grams) were used as experimental animals. Animals were housed individually in polypropylene cages. Two days prior to study, male Wistar rats were anesthetized with isoflurane for surgical placement of jugular vein catheter. Rats were randomly divided for oral (3 mg/kg and 10 mL/kg as dose volume) and intravenous (1 mg/kg and 2.0 mL/kg as dose volume) dosing (n=3/group) and fasted overnight before oral dosing (p.o.). However, rats allocated to intravenous dosing food and water was provided ad libitum.

Intravenous formulation was prepared by using 5% Pharmasolve+45% Propylene Glycol+50% PEG 400 as vehicle. For Oral, formulation was prepared by using 0.25% Tween 80+99.75% of 1% (w/v) hydroxyethylcellulose solution as a vehicle. The dose formulations were prepared freshly on the day of dosing.

After dosing of animal, each time point a 200 µL of blood sample was collected through the jugular vein and replenished with an equivalent volume of normal saline. Collected blood sample was transferred into a labeled eppendorf tube containing 10 µL of sodium heparin (1000 IU/mL) as an anticoagulant. Typically blood samples were collected at following time points: 0.08, 0.25, 0.5, 1, 2, 4, 6, 8, and 24 h post dose. Blood was centrifuged at 4000 revolutions per minute (rpm) for 10 min. Plasma was separated and stored frozen at −80° C. until analysis. The concentrations of the test compounds were quantified in plasma by qualified LC-MS/MS method using suitable extraction technique in the calibration range around 1-2000 ng/mL in plasma. Study samples were analyzed using calibration samples in the batch and quality control samples spread across the batch. Pharmacokinetic parameters $C_{max}$, AUC$_{0-t}$, $t_{1/2}$, Clearance and Bioavailability (F) were calculated using standard non-compartmental model by using Phoenix WinNonlin 8.1 version Software package.

TABLE 2

Pharmacokinetic profile of the test compounds

| Example No. | ROA | $C_{max}$ (ng/mL) | AUC$_{0-t}$ (ng · hr/mL) | $t_{1/2}$ (hr) | F (%) |
|---|---|---|---|---|---|
| 2 | oral (gavage) | 724 ± 170 | 795 ± 34.5 | — | 46 ± 2 |
|  | intravenous (bolus) | — | 575 ± 60.8 | 1.98 ± 0.96 |  |
| 12 | oral (gavage) | 279 ± 59.2 | 250 ± 60 | — | 18 ± 4.3 |
|  | intravenous (bolus) | — | 467 ± 115 | 2.59 ± 0.49 |  |

Example-50: Rodent Brain Penetration Study

Male Wistar rats (260±40 g) were used as experimental animals. Three animals were housed in each cage. Animals were given water and food ad libitum throughout the experiment and maintained on a 12 h light/dark cycle.

Brain penetration was determined in discrete manner in rats. One day prior to dosing day, male Wistar rats were acclimatized and randomly grouped according to their weight. At each time point (0.50, 1 and 2 h) n=3 animals were used.

The test compounds were suitably preformulated and administered orally at (free base equivalent) 3 mg/kg. Blood samples were removed via cardiac puncture by using isoflurane anesthesia. The animals were sacrificed to collect brain tissue. Plasma was separated and brain samples were homogenized and stored frozen at −20° C. until analysis. The concentrations of the test compounds in plasma and brain were determined using LC-MS/MS method.

The test compounds were quantified in plasma and brain homogenate by qualified LC-MS/MS method using suitable extraction technique in the calibration range of 1-2000 ng/mL. Study samples were analyzed using calibration samples in the batch and quality control samples spread across the batch. Extent of brain-plasma ratio ($C_{brain}/C_{plasma}$) was calculated

TABLE 3

Blood-Brain Penetration data of the test compounds

| Example No. | Rat Brain Penetration ($C_{brain}/C_{plasma}$) at 3 mg/kg, p.o. @ 1 h |
|---|---|
| 2 | 1.25 |
| 12 | 2.09 |

Example-51: Amphetamine-Induced Open Filed Assay

Male Wistar rats of 230-250 g weight were used. The body weights of the rats were recorded. Rats were randomized according to their body weights. Animals were brought to the laboratory 1 h prior to acclimatizing to the laboratory conditions. The open field is black colored arena of 51×51× 51 cm enclosed by black plastic walls of same dimensions. Rats were habituated to the open field arena for a period of 15 min. Animals were administered respective treatments (Vehicle or Example-2) 60 min prior to the trial. After 30 min, animals were challenged with amphetamine (2.5 mg/kg, i.p.) or vehicle. Then the animals were placed in open field arenas and distance traveled by mice was tracked for 15 min using Videomot software. Data was analyzed using GraphPad prism.

Results: Rats treated with all the doses of Example-2 (3, 10, 30 mg/kg, p.o) showed significant decrease in locomotion when compared with Amphetamine (2.5 mg/kg, i.p.) treated group. Example-2 antagonized the effect of Amphetamine on locomotion in rats. Results suggest Example-2 may have potential utility for the treatment of schizophrenia (FIG. 1).

Example-52: Rat Rotarod Assay

The rotarod test was employed to investigate the possible effect of Example-2 on motor coordination. Twenty hours prior to the test, rats were trained to remain on revolving bar (4 rpm) of the rotarod apparatus (TSE Systems; GmHb, Germany). Animals that successfully stayed on rotating rod for 60 seconds (out of 4 trials per animal) were selected for further study. Animals that did not complete 60 seconds stay within 4 choices were rejected from the study. A single trial was carried out on the next day. Animals that were able to stay on the rotating rod for 60 seconds were chosen for further study. Animals were administered Example-2 or Vehicle 60 min prior to the trial. The latency to fall from the rotating rod was noted.

Figure 2:
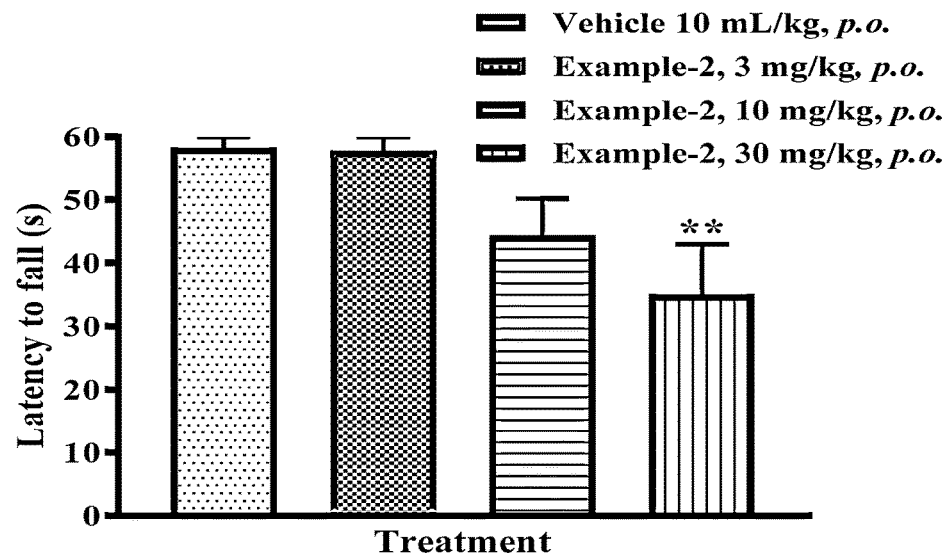
FIG. 2: Effect of Example-2 in rotarod assay

Results: No notable effects on motor coordination were observed at doses of 3 & 10 mg/kg, suggesting separation between doses that result in efficacy, and side effects (FIG. 2).

Example-53: Reserpine-Induced DOPA Accumulation

Male Wistar rats were pretreated with reserpine (5 mg/kg, s.c.) approximately 18 h before sacrifice and were thereafter fasted until sacrifice. Example-2 (3 mg/kg, p.o.) and (3-(3-hydroxyphenyl)-N-n-propylpiperidine (3-PPP); 30 mg/kg, s.c.) were administered 1.16 h and 1 h, respectively before sacrifice. Haloperidol (0.5 mg/kg, s.c.) was used as a positive control and was dosed 10 min prior to 3-PPP in a separate group of animals. 3-Hydroxybenzylhydrazine dihydrochloride (NSD-1015; 100 mg/kg, s.c.) was then administered 0.5 h before sacrifice. Each rat was sacrificed, brain was removed and then striatum was isolated. The tissue was immediately weighed and homogenized in 0.1 N perchloric acid by means of an ultrasonic disruptor while being cooled in ice. The homogenate was centrifuged at 4° C. at 20,000 g for 15 min. The supernatant was assayed for dihydroxyphenylalanine (DOPA) levels using HPLC-ECD.

Figure 3:
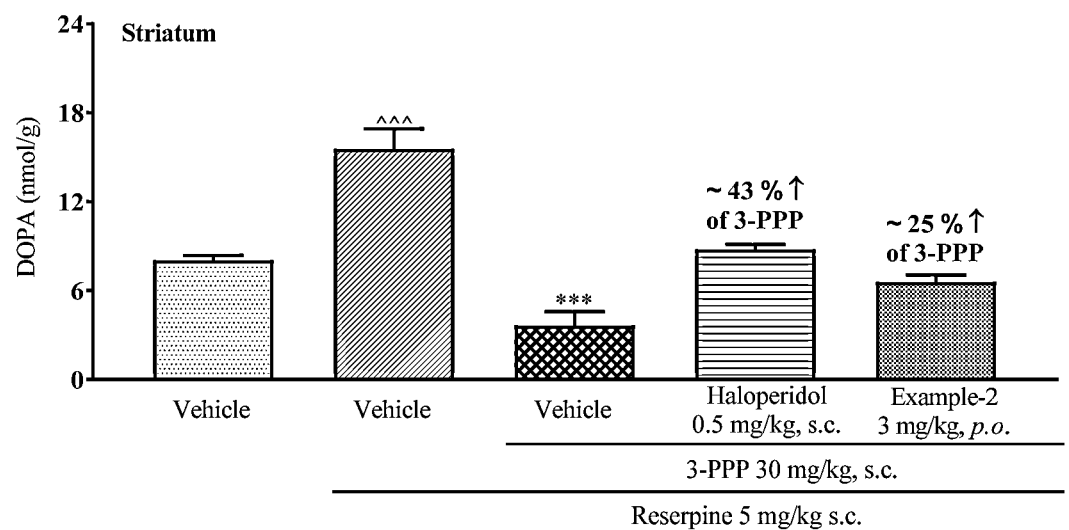
FIG. 3: Effect of Example-2 on 3-PPP and reserpine induced DOPA levels in striatum

Results: Treatment with reserpine produced about 194% increase in DOPA levels in striatum. However, 3-PPP, an agonist at dopamine receptor produced 77% reversal in reserpine induced DOPA accumulation. A pretreatment with Example-2 produced 25% blockade of the effects of 3-PPP. Results from the current study indicate that Example-2 might behave as a partial agonist in vivo at dopamine $D_2$ receptor (FIG. 3).

We claim:

1. A compound of formula (I),

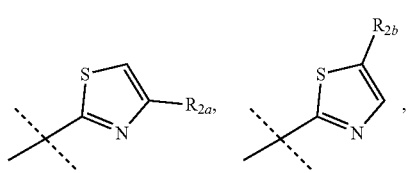

or an isotopic form, a stereoisomer, or a pharmaceutically acceptable salt thereof,
wherein,
A is O or S;
R is N or CH;
Y is selected from —$CH_2$—, —O—, NH, or —N($C_{1-4}$ alkyl)-;
n is an integer from 0 to 2;
$R_1$ is selected from:

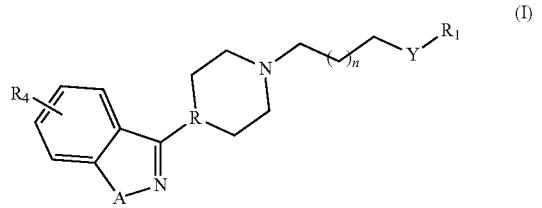

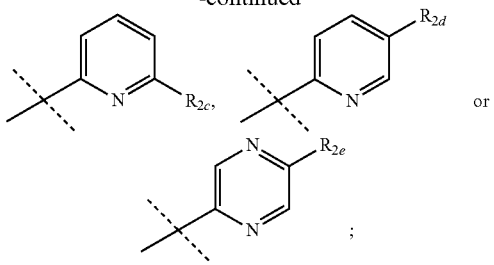

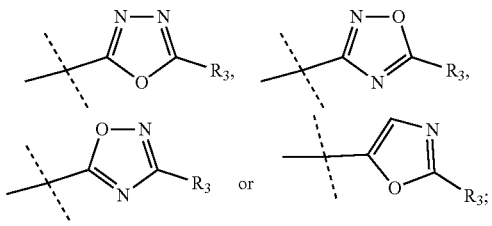

wherein, $R_{2a}$, $R_{2b}$, $R_{2c}$, $R_{2d}$ and $R_{2e}$ are each independently selected from:

"------" represents the point of attachment;
$R_3$ at each occurrence is independently selected from hydrogen, —($C_{1-4}$)alkyl, or —($C_{3-6}$) cycloalkyl; and
$R_4$ is selected from hydrogen, halogen, —($C_{1-4}$)alkyl, —($C_{3-6}$) cycloalkyl or hydroxy-($C_{1-4}$)alkyl.

2. The compound of formula (I) or an isotopic form, a stereoisomer, or a pharmaceutically acceptable salt thereof as claimed in claim 1, is selected from:
3-(4-{3-[4-(5-Methyl-[1,3,4]oxadiazol-2-yl)-thiazol-2-yloxy]-propyl}-piperazin-1-yl)-benzo[d]isothiazole;
3-(4-{2-[4-(5-Methyl-[1,3,4]oxadiazol-2-yl)-thiazol-2-yloxy]-ethyl}-piperazin-1-yl)-benzo[d]isothiazole;
3-(4-{3-[4-(5-Cyclopropyl-[1,3,4]oxadiazol-2-yl)-thiazol-2-yloxy]-propyl}-piperazin-1-yl)-benzo[d]isothiazole;
3-(4-{3-[5-(5-Methyl-[1,3,4]oxadiazol-2-yl)-thiazol-2-yloxy]-propyl}-piperazin-1-yl)-benzo[d]isothiazole;
3-(4-{3-[4-(5-Methyl-[1,2,4]oxadiazol-3-yl)-thiazol-2-yloxy]-propyl}-piperazin-1-yl)-benzo[d]isothiazole;
3-(4-{3-[4-(3-Methyl-[1,2,4]oxadiazol-5-yl)-thiazol-2-yloxy]-propyl}-piperazin-1-yl)-benzo[d]isothiazole;
3-{4-[3-(4-Oxazol-5-yl-thiazol-2-yloxy)-propyl]-piperazin-1-yl}-benzo[d]isothiazole;
3-(4-{3-[6-(5-Methyl-[1,2,4]oxadiazol-3-yl)-pyridin-2-yloxy]-propyl}-piperazin-1-yl)-benzo[d]isothiazole;
3-(4-{3-[5-(5-Methyl-[1,2,4]oxadiazol-3-yl)-pyridin-2-yloxy]-propyl}-piperazin-1-yl)-benzo[d]isothiazole;
3-(4-{3-[5-(5-Methyl-[1,2,4]oxadiazol-3-yl)-pyrazin-2-yloxy]-propyl}-piperazin-1-yl)-benzo[d]isothiazole;
3-{4-[3-(5-Oxazol-5-yl-pyridin-2-yloxy)-propyl]-piperazin-1-yl}-benzo[d]isothiazole;
6-Fluoro-3-(1-{3-[4-(5-methyl-[1,3,4]oxadiazol-2-yl)-thiazol-2-yloxy]-propyl}-piperidin-4-yl)-benzo[d]isoxazole;
6-Fluoro-3-(1-{3-[5-(5-methyl-[1,3,4]oxadiazol-2-yl)-thiazol-2-yloxy]-propyl}-piperidin-4-yl)-benzo[d]isoxazole;
6-Fluoro-3-(1-{3-[4-(5-methyl-[1,2,4]oxadiazol-3-yl)-thiazol-2-yloxy]-propyl}-piperidin-4-yl)-benzo[d]isoxazole;

6-Fluoro-3-(1-{3-[4-(3-methyl-[1,2,4]oxadiazol-5-yl)-thiazol-2-yloxy]-propyl}-piperidin-4-yl)-benzo[d]isoxazole;

6-Fluoro-3-{1-[3-(4-oxazol-5-yl-thiazol-2-yloxy)-propyl]-piperidin-4-yl}-benzo[d]isoxazole;

6-Fluoro-3-{1-[3-(5-oxazol-5-yl-pyridin-2-yloxy)-propyl]-piperidin-4-yl}-benzo[d]isoxazole;

3-(4-{3-[6-(5-Methyl-[1,3,4]oxadiazol-2-yl)-pyridin-2-yloxy]-propyl}-piperazin-1-yl)-benzo[d]isothiazole;

3-(4-{3-[6-(3-Methyl-[1,2,4]oxadiazol-5-yl)-pyridin-2-yloxy]-propyl}-piperazin-1-yl)-benzo[d]isothiazole;

3-{4-[3-(4-[1,2,4]oxadiazol-3-yl-thiazol-2-yloxy)-propyl]-piperazin-1-yl}-benzo[d]isothiazole; or 3-{4-[3-(6-[1,2,4]Oxadiazol-3-yl-pyridin-2-yloxy)-propyl]-piperazin-1-yl}-benzo[d]isothiazole.

3. The compound of formula (I), or an isotopic form, a stereoisomer, or a pharmaceutically acceptable salt thereof as claimed in claim 1, is selected from:

3-(4-{3-[4-(5-Methyl-[1,3,4]oxadiazol-2-yl)-thiazol-2-yloxy]-propyl}-piperazin-1-yl)-benzo[d]isothiazole oxalate;

3-(4-{2-[4-(5-Methyl-[1,3,4]oxadiazol-2-yl)-thiazol-2-yloxy]-ethyl}-piperazin-1-yl)-benzo[d]isothiazole oxalate;

3-(4-{3-[4-(5-Cyclopropyl-[1,3,4]oxadiazol-2-yl)-thiazol-2-yloxy]-propyl}-piperazin-1-yl)-benzo[d]isothiazole oxalate;

3-(4-{3-[5-(5-Methyl-[1,3,4]oxadiazol-2-yl)-thiazol-2-yloxy]-propyl}-piperazin-1-yl)-benzo[d]isothiazole oxalate;

3-(4-{3-[4-(5-Methyl-[1,2,4]oxadiazol-3-yl)-thiazol-2-yloxy]-propyl}-piperazin-1-yl)-benzo[d]isothiazole oxalate;

3-(4-{3-[4-(3-Methyl-[1,2,4]oxadiazol-5-yl)-thiazol-2-yloxy]-propyl}-piperazin-1-yl)-benzo[d]isothiazole oxalate;

3-{4-[3-(4-Oxazol-5-yl-thiazol-2-yloxy)-propyl]-piperazin-1-yl}-benzo[d]isothiazole oxalate;

3-(4-{3-[6-(5-Methyl-[1,2,4]oxadiazol-3-yl)-pyridin-2-yloxy]-propyl}-piperazin-1-yl)-benzo[d]isothiazole oxalate;

3-(4-{3-[5-(5-Methyl-[1,2,4]oxadiazol-3-yl)-pyridin-2-yloxy]-propyl}-piperazin-1-yl)-benzo[d]isothiazole oxalate;

3-(4-{3-[5-(5-Methyl-[1,2,4]oxadiazol-3-yl)-pyrazin-2-yloxy]-propyl}-piperazin-1-yl)-benzo[d]isothiazole oxalate;

3-{4-[3-(5-Oxazol-5-yl-pyridin-2-yloxy)-propyl]-piperazin-1-yl}-benzo[d]isothiazole oxalate;

6-Fluoro-3-(1-{3-[4-(5-methyl-[1,3,4]oxadiazol-2-yl)-thiazol-2-yloxy]-propyl}-piperidin-4-yl)-benzo[d]isoxazole oxalate;

6-Fluoro-3-(1-{3-[5-(5-methyl-[1,3,4]oxadiazol-2-yl)-thiazol-2-yloxy]-propyl}-piperidin-4-yl)-benzo[d]isoxazole oxalate;

6-Fluoro-3-(1-{3-[4-(5-methyl-[1,2,4]oxadiazol-3-yl)-thiazol-2-yloxy]-propyl}-piperidin-4-yl)-benzo[d]isoxazole oxalate;

6-Fluoro-3-(1-{3-[4-(3-methyl-[1,2,4]oxadiazol-5-yl)-thiazol-2-yloxy]-propyl}-piperidin-4-yl)-benzo[d]isoxazole oxalate;

6-Fluoro-3-{1-[3-(4-oxazol-5-yl-thiazol-2-yloxy)-propyl]-piperidin-4-yl}-benzo[d]isoxazole oxalate;

6-Fluoro-3-{1-[3-(5-oxazol-5-yl-pyridin-2-yloxy)-propyl]-piperidin-4-yl}-benzo[d]isoxazole oxalate;

3-(4-{3-[6-(5-Methyl-[1,3,4]oxadiazol-2-yl)-pyridin-2-yloxy]-propyl}-piperazin-1-yl)-benzo[d]isothiazole oxalate;

3-(4-{3-[6-(3-Methyl-[1,2,4]oxadiazol-5-yl)-pyridin-2-yloxy]-propyl}-piperazin-1-yl)-benzo[d]isothiazole oxalate;

3-{4-[3-(4-[1,2,4]oxadiazol-3-yl-thiazol-2-yloxy)-propyl]-piperazin-1-yl}-benzo[d]isothiazole oxalate; or 3-{4-[3-(6-[1,2,4]Oxadiazol-3-yl-pyridin-2-yloxy)-propyl]-piperazin-1-yl}-benzo[d]isothiazole oxalate.

4. A pharmaceutical composition comprising a therapeutically effective amount of the compound of formula (I), or a stereoisomer, or a pharmaceutically acceptable salt thereof as claimed in claim 1, and pharmaceutically acceptable excipients or carriers.

5. A method of treating disease or disorder selected from schizophrenia, psychosis, bipolar disorder, mood disorders, depression, anxiety, sleep disorders, sexual disorders, drug dependency withdrawal symptoms, attention deficit hyperactivity disorder, neuropsychiatric disorders associated with Alzheimer's disease, Parkinson's disease, Lewy body dementia, Frontotemporal dementia, or vascular dementia, comprising the step of administering to a patient in need thereof, a therapeutically effective amount of the compound of formula (I), or an isotopic form, a stereoisomer, or a pharmaceutically acceptable salt thereof as claimed in claim 1.

* * * * *